US006790841B2

(12) United States Patent
Zemlicka et al.

(10) Patent No.: US 6,790,841 B2
(45) Date of Patent: *Sep. 14, 2004

(54) 2-HYDROXYMETHYLCYCLO-PROPYLIDENEMETHYLPURINES AND -PYRIMIDINES AS ANTIVIRAL AGENTS

(75) Inventors: Jiri Zemlicka, Warren, MI (US); Yao-Ling Qiu, Detroit, MI (US); John C. Drach, Ann Arbor, MI (US); Roger G. Ptak, New Market, MD (US)

(73) Assignees: Wayne State University, Detroit, MI (US); The Regents of the University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/047,202

(22) Filed: Jan. 14, 2002

(65) Prior Publication Data

US 2002/0193353 A1 Dec. 19, 2002

Related U.S. Application Data

(63) Continuation of application No. 09/267,839, filed on Mar. 12, 1999, now Pat. No. 6,352,991, which is a continuation-in-part of application No. PCT/US98/00440, filed on Jan. 7, 1998.
(60) Provisional application No. 60/035,826, filed on Jan. 8, 1997, and provisional application No. 60/045,676, filed on May 6, 1997.

(51) Int. Cl.[7] ................. C07D 473/40; C07D 473/16; C07D 473/34; C07D 373/18; A61K 31/52
(52) U.S. Cl. .............. 514/81; 514/151; 514/263.3; 514/263.34; 514/263.37; 514/263.4; 544/244; 544/264; 544/265; 544/276; 544/277; 544/280; 544/254; 544/317; 544/309; 544/182; 546/118
(58) Field of Search ................. 544/244, 276, 544/277, 264, 265, 267; 514/151, 263.3, 263.34, 263.37, 263.4, 81

(56) References Cited

U.S. PATENT DOCUMENTS 4,935,427 A  6/1990 Broder ............... 514/261
6,352,991 B1 * 3/2002 Zemlicka et al. ......... 544/276

FOREIGN PATENT DOCUMENTS

WO      WO 98/30563 A1    7/1998

OTHER PUBLICATIONS

Ashton, W.T. et al., "Synthesis and antiherpetic activity of +−(−)−9−[[(Z)−2−(hydroxymethyl)cyclopropyl]methyl]guanine and related compounds," J. Med. Chem. 31:2304–2315 (1988).

(List continued on next page.)

Primary Examiner—Mark L. Berch
(74) Attorney, Agent, or Firm—DeAnn F. Smith; Lahive & Cockfield LLP

(57) ABSTRACT

Compounds which are active against viruses have the following Formulas:

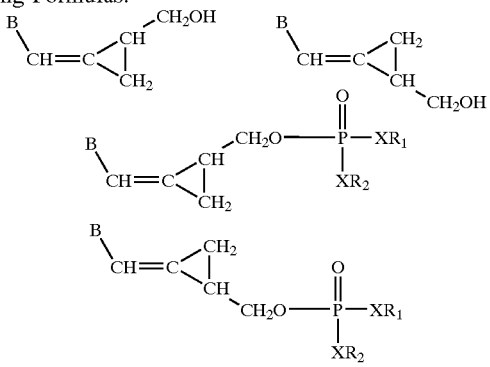

wherein B is a purine or pyrimidine heterocyclic ring and is preferably selected from the group consisting of 6-aminopurine (adenine), 2,6-diaminopurine, 2-amino-6-azidopurine, 2-amino-6-cyclopropylaminopurine, 6-hydroxypurine (hypoxanthine), 2-amino-6-halo substituted purines, 2-amino-6-alkoxy substituted purines, 2-amino-6-hydroxypurine (guanine), 3-deazapurines, 7-deaza-purines, 8-azapurines, cytosine, 5-halo substituted cytosines, 5-alkyl substituted cytosines, thymine, uracil and 6-azapyrimidines; X is O; and, $R_1$ and $R_2$ are alkyl or aryl groups. The compounds of the present invention also include the R- and S-enantiomers of the above compounds. The $R_1X$ and/or $R_2X$ can also be amino acid residues with X as NH.

19 Claims, 5 Drawing Sheets

OTHER PUBLICATIONS

De Clercq, E., "Toward improved anti–HIV chemotherapy: theraupetic strategies for intervention with HIV infections," J. Med. Chem., 38:2491–2517 (1995).

Doyle, M.P. et al. "Highly effective catalytic methods for ylide generation from Diazo compounds. Mechanism of the rhodium—and copper–catalyzed reactions with allylic compounds" J. Org. Chem. 46:5094–5102 (1981).

Dyakonov, I.A. et al. "Reactions of aliphatic diazo–compounds with unsaturated compounds" J. Gen. Chem. USSR (English translation) 25:1435–1440 (1955).

Franchetti, P. et al. "Synthesis and evaluation of the anti–HIV activity of aza and deasa analogues of isoddA and their phosphates as prodrugs," J. Med. Chem. 37:3534–3541 (1994).

Harnden, M.R. et al. "Synthesis and antiviral activity of 9–alkoxypurines. 1. 9–(3–Hydroxypropoxy)– and 9–[3–hydroxymethyl)propoxy]purines," J. Med. Chem. 33:187–196 (1990).

Kucera, L.S. et al. "Activity of triciribine and triciribine–5'–monophosphate against human immunodeficiency virus types 1 and 2," AIDS Res. Human retroviruses 9:307–314 (1993).

Lai, M.–T. et al "Mechanistic study on the inactivation of general acyl–CoA dehydrogenase by a metabolite of hypoglycin A" Am. Chem. Soc. 113:7388–7397 (1991).

Larsson, A. et al., "Mode of action, toxicity, pharmacokinetics, and efficacy of some new antiherpesvirus guanosine analogs related to buciclovir," Antimicrob. Agents& Chemother, 30:598–605 (1986).

Levine, A.J. Viruses, Ch. 4, W.H. Freeman & Co., New York, pp. 67–85 (1992).

McGuigan, C. et al., "Aryl phosphate derivatives of AZT retain activity against HIV1 in cell lines which are resistant to the action of AZT," Antiviral Res. 17:311–321 (1992).

McGuigan, C. et al., "Intracellular delivery of bioactive AZT nucleotides by aryl phosphate derivatives of AZT," J. Med. Chem. 36:1048–1052 (1993).

Otter, B.A. et al. "N–acyl derivatives of 2'–deoxyctidine in synthetic procedures in nucleic acid chemistry," vol. 1, John Wiley & Sons, New York, pp. 285–287 (1967).

Prichard, M.N. et al. "A microtiter virus yield reduction assay for the evaluation of antiviral compounds against human cytomegalovirus and herpes simplex virus," J. Virol. Methods, 28:101–106 (1990).

Prichard, M.N. et al. "Three–dimensional analysis of the synergistic cytotoxicity of ganciclovir and zidovudine," Antimicrob. Agents Chemother 35:1060–1065 (1991).

Qiu, Y.–L. "A new efficient synthesis of antiviral methylenecyclopropane analogs of purine nucleosides" J. Synthesis 1447–1452 (1998).

Qiu, Y.–L. "(Z–) and (E)–2–((hydroxymethyl) cyclopropylidene) methyladenine and –guanine. New nucleoside analogs with a broad–spectrum antivral activity," J. Med. Chem, 41;10–23 (1998).

Qiu, Y.–L. et al. Synthesis and antiviral activity of phosphoralaninate derivatives of methylenecyclopropane analogues of nucleosides. Antiviral Res. 43(1):37–53 (1999).

Rybak RJ, et al. "Effective treatment of murine cytomegalovirus infections with methylenecyclopropane analogues of nucleosides." Antiviral Res. 43(3):165–178 (1999).

Shipman, C. "Evaluation of 4–(2–hydroxyethyl)–1–piperazineethanesulfonic acid (HEPES) as a tissue culture buffer," Proc. Soc. Exp. Biol. Med. 130:305–310 (1969).

Turk, S.R. et al. "Pyrrolo[2,3–d]pyrimidine nucleosides as inhibitors of human cytomegalovirus," Antimicrob. Agents Chemother 31:544–550 (1987).

White, E.L. et al "A TIBO deriviative, R82913, is a potent inhibitor of HIV–1 reverse transcriptase with heteropolymer templates," Antiviral Res. 16:257–266 (1991).

Zemlicka, J. et al. "Preparation of N–dimethylaminomethylene derivatives; A new method of a selective substitution of nucleoside amino groups," Collect. Czech. Chem. Commun. 32:3159–3168 (1967).

Zemlicka, J. "Allenols derived from nucleic acid bases—A new class of anti–HIV agents: Chemistry and biological activity in nucleosides and nucleotides as antitumor and antiviral agents," (Chu, Baker, Eds.), Plenum Press, New York, pp. 73–100 (1993).

"Relationship between the human immunodeficiency virus and the acquired immunodeficiency syndrome," The national institute of allergy and infectious diseases, National Institutes of Health, Bethesda, Maryland, pp. 1–3 (1995).

* cited by examiner

DMF = N,N-Dimethylformamide
DIBAH = Diisobutylaluminum hydride
THF = Tetrahydrofuran
tBuOK = Potassium tert.-butoxide

2-HYDROXYMETHYLCYCLO-PROPYLIDENEMETHYLPURINES AND -PYRIMIDINES AS ANTIVIRAL AGENTS

RELATED APPLICATIONS

The present invention is a continuation of U.S. Ser. No. 09/267,839, filed Mar. 12, 1999; now U.S. Pat. No. 6,352,991 which is a continuation-in-part of PCT International Application No. PCT/US98/00440, filed Jan. 7, 1998, designating the United States, which claims priority from U.S. Serial No. 60/035,826, filed Jan. 8, 1997 and U.S. Serial No. 60/045,676, filed May 6, 1997, all of which are hereby expressly incorporated by reference.

SPONSORSHIP

Work on this invention was supported in part by the National Cancer Institute, Grant No. RO1 CA32779 and National Institute Of Allergy And Infectious Diseases, Grant Nos. U19 Al 31718 and RO1 A133332. The Government has certain rights in the invention.

FIELD OF THE INVENTION

The present invention relates generally to novel purine and pyrimidine compounds which have antiviral activity and methods of making and using same.

BACKGROUND OF THE INVENTION

Viruses are the etiologic cause of many life-threatening human diseases. Of special importance are herpes viruses such as herpes simplex 1 (HSV-1), herpes simplex 2 (HSV-2), cytomegalovirus (CMV), Epstein-Barr virus (EBV), varicella zoster virus (VZV) and human herpes virus 6 (HHV 6) which are associated with many common viral illnesses. The HSV-1 and HSV-2 infections are characterized by cold sores of skin, mouth or genital region. After primary infection the virus is harbored in neural cells and can reappear later in the life of a patient. Human CMV (HCMV) infection is a life-long affliction which can result in morbidity and mortality. These pathologies include microcephaly, hepatosplenomegaly, jaundice, encephalitis, infections of the newborn infants or fetuses in utero, and infections of immunocompromised hosts. The HCMV infection is responsible for retinitis, gastritis and pneumonitis in AIDS patients and HCMV-induced pneumonias or hepatitis are frequent and serious complications of bone marrow transplants. EBV causes infectious mononucleosis and it is considered as the etiologic agent of nasopharyngeal cancer, immunoblastic lymphoma, Burkitt's lymphoma and hairy leukoplakia. VZV causes chicken pox and shingles. Although in children the chicken pox is usually a non-fatal disease, the recurrent form of this infection, shingles, may in advanced stage lead to paralysis, convulsions and ultimately death. Again, in immunocompromised patients the infection with VZV is a serious complication. Human herpes virus 6 (HHV-6) which is commonly associated with children's rash was also identified in acquired immunodeficiency syndrome (AIDS) patients and it may be a cofactor in the pathogenesis of AIDS in hosts infected with human immunodeficiency virus (HIV). Levine, A. J., *Viruses*, Ch. 4, W. H. Freeman & Co., New York, pp. 67–85 (1992); *Human Herpesvirus Infections*, Raven Press, New York (1986).

HIV is the underlying cause of AIDS, a world-wide epidemic with fatal consequences. According to the World Health Organization, over 4.5 million AIDS cases were recorded by late 1994 and 19.5 million people had been infected with HIV. It is estimated that by the year 2000, 30 to 40 million will have been infected with HIV with 10 million cases of full-blown AIDS. Estimates of Global AIDS Policy Coalition are considerably higher—up to 110 million HIV infections and 25 million AIDS cases. *The Relationship between the Human Immunodeficiency Virus and the Acquired Immunodeficiency Syndrome*, The National Institute of Allergy and Infectious Diseases, National Institutes of Health, Bethesda, Md., pp. 1–3 (1995).

Various alkyl derivatives of purines and pyrimidines and analogues thereof have been found to exhibit antiviral activity. Notably, acyclovir (Zovirax) and ganciclovir (Cytovene) belonging to this group of compounds are approved drugs for infections caused by HSV-1, HSV-2, VZV and HCMV. *Acyclovir Therapy for Herpesvirus Infections* (Baker, Ed.), M. Dekker, New York, (1990); *Ganciclovir Therapy for Cytomegalovirus Infection* (Spector, S. S., Ed.), M. Dekker, New York (1991). A considerable effort went into design, synthesis and biological investigation of analogues of these drugs as well as in development of new antiviral agents. Larsson, A., et al., *Antimicrob. Agents & Chemother.* 30:598–605 (1986); Ashton, W. T., et al., *J. Med. Chem.* 31:2304–2315 (1988).

Current drugs for AIDS include AZT (zidovudine, Retrovir), ddI (didanosine, Videx), ddC (zalcitabine, Hivid) and d4T (stavudine, Zerit). De Clercq, E., *J. Med. Chem.* 38:2491–2517 (1995). Allenic nucleoside analogues such as adenallene and cytallene are examples of anti-HIV agents containing an unsaturated alkyl group. U.S. Pat. No. 4,935,427; Zemlicka, J., *Allenols Derived from Nucleic Acid Bases—a New Class of Anti-HIV Agents:Chemistry and Biological Activity in Nucleosides and Nucleotides as Antitumor and Antiviral Agents* (Chu, C. K.; Baker, D. C., Eds.), Plenum Press, New York, pp. 73–100 (1993).

It would thus be desirable to provide novel compounds which are active against viruses, including HCMV, HSV-1, HSV-2, HHV-6, HIV, hepatitis B virus (HBV), and other mammalian viruses.

SUMMARY OF THE INVENTION

The present invention provides novel 2-hydroxymethylcyclopropylidenemethyl-derivatives of heterocyclic compounds, prodrugs and pharmacologically acceptable acid salts thereof. These compounds have been found to be useful antiviral agents and are effective against HCMV, HSV-1, HSV-2, HHV-6, HIV, EBV and HBV, as well as against other mammalian viruses.

The compounds of the present invention have the following Formulas:

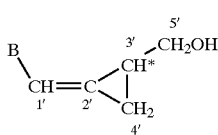

Formula 1

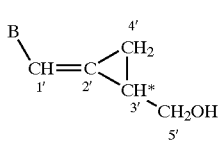

Formula 2 wherein

B is a heterocyclic ring derived from a purine or pyrimidine moiety. In a preferred embodiment, the purine moieties include 6-aminopurine (adenine), 2,6-diaminopurine, 2-amino-6-azidopurine, 2-amino-6-thiopurine, 2-amino-6-alkylaminopurines such as 2-amino-6-cyclopropylaminopurine, 6-hydroxypurine (hypoxanthine), 2-amino-6-halo substituted purines, such as 2-amino-6-chloropurine, 2-amino-6-alkoxy substituted purines, such as 2-amino-6-methoxypurine, 2-amino-6-hydroxypudne (guanine), 3-deazapurines, 7-deazapurines, 8-azapurines, cytosine, 5-halo substituted cytosines, 5-alkyl substituted cytosines, thymine, uracil and 6-azapyrimidines.

Prodrugs of the antiviral nucleoside analogues of the present invention include lipophilic phosphate esters or amidates capable of penetrating the cell membrane. Those skilled in the art will appreciate that the aim of prodrugs is to provide effective therapeutic agents for resistant strains of viruses (McGuigan, C., et al., *J. Med. Chem.* 36:1048–1052 (1993)) or activate inactive analogues. Franchetti, P., et al., *J. Med. Chem.* 37:3534–3541 (1994).

The compounds of the present invention therefore also include prodrugs of the novel compounds, wherein the prodrugs have the following Formulas:

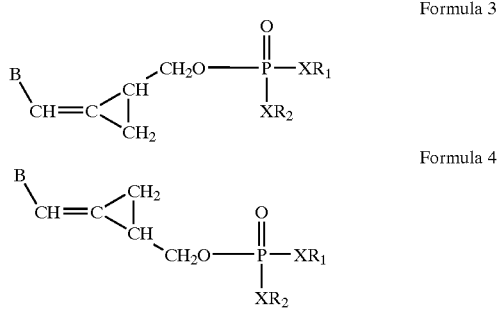

Formula 3

Formula 4 wherein

B is a heterocyclic ring as defined above for Formulas 1 and 2;

X is O; and $R_1$ and $R_2$ are alkyl or aryl. The $R_1X$ or $R_2X$ may also be amino acid residues with X as NH.

Compositions useful for treating viral infections, such as HCMV, HSV-1, HSV-2, HHV-6, HIV, EBV and HBV contain an effective amount of at least one compound of Formulas 1 to 4 or a pharmaceutically acceptable salt thereof.

The present invention also includes methods for synthesizing compounds of Formulas 1 and 2 wherein B is a heterocyclic ring derived from purine or pyrimidine moiety such as 6-aminopurine (adenine), 2,6-diaminopurine, 2-amino-6-azidopurine, 2-amino-6-thiopurine, 2-amino-6-alkylaminopurines such as 2-amino-6-cyclopropylaminopurine, 6-hydroxypurine (hypoxanthine), 2-amino-6-halo substituted purines, such as 2-amino-6-chloropurine, 2-amino-6-alkoxy substituted purines, such as 2-amino-6-methoxypurine, 2-amino-6-hydroxypurine (guanine), 3- and 7-deazapurines, such as 3- and 7-deazaadenine, 8-azapurines such as 8-azaadenine, cytosine, 5-halocytosine (wherein halo is bromo, chloro, iodo or fluoro) and related alkyl derivatives containing a saturated or unsaturated alkyl group at the 5-position, thymine, uracil, 6-azapyrimidines such as 6-azacytosine, wherein the alkyl side-chain attached to the heterocyclic ring is a 2-hydroxymethylcyclopropyiidenemethane moiety.

The present invention also provides methods for synthesizing prodrugs of the compounds as set forth in Formulas 3 and 4.

The present invention also provides methods for synthesizing essentially enantiomerically pure R- and S-enantiomers of the compounds of the present invention.

Additional objects, advantages, and features of the present invention will become apparent from the following description, taken in conjunction with the accompanying drawings.

BRIEF DESCRIPTION OF THE DRAWINGS

The various advantages of the present invention will become apparent to one skilled in the art by reading the following specification and by referencing the following drawings in which:

FIG. 4 also shows the synthesis of syn-2,6-diamino-$N^9$-(2-hydroxymethylcyclopropylidenemethyl)purine (1, B=2,6-diaminopurine) and syn-2-amino-6-cyclopropylamino-$N^9$-(2-hydroxymethylcyclopropylidenemethyl)purine (1, B=2-amino-6-cyclopropylaminopurine) from syn-2-amino-6-chloro-$N^9$-(2-hydroxymethylcyclopropylidenemethyl)purine (1, B=2-amino-6-chloro-purine);

DETAILED DESCRIPTION OF THE PREFERRED EMBODIMENTS

Figure 1:
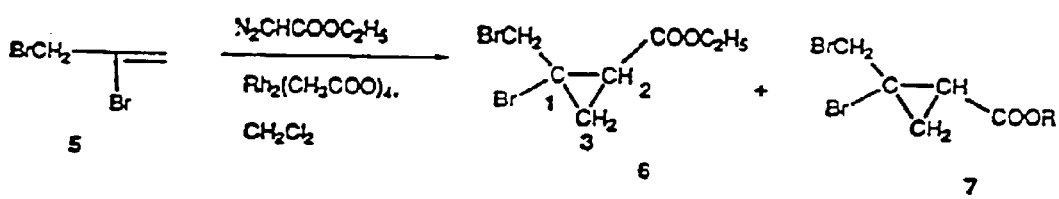
FIG. 1 shows the synthesis of the mixture of cis-ethyl 2-bromo-2-bromo-methylcyclopropane 1-carboxylate (6) and trans-ethyl 2-bromo-2-bromomethylcyclo-propane 1-carboxylate (7)

The compounds of the present invention which have been found to be effective against herpes viruses, human immunodeficiency virus, and hepatitis B virus, are compounds of Formulas 1 to 4, wherein B represents a heterocyclic ring derived from purine or pyrimidine moiety such as 6-aminopurine (adenine), 2,6-diaminopurine, 2-amino-6-azidopurine, 2-amino-6-thiopurine, 2-amino-6-alkylaminopurines such as 2-amino-6-cyclopropylaminopurine, 6-hydroxypurine (hypoxanthine), 2-amino-6-halo substituted purines, such as 2-amino-6-chloropurine, 2-amino-6-alkoxy substituted purines, such as 2-amino-6-methoxypurine, 2-amino-6-hydroxypurine (guanine), 3- and 7-deazapurines, such as 3- and 7-deazaadenine, 8-azapurines such as 8-azaadenine, cytosine, 5-halocytosine (wherein halo is bromo, chloro, iodo, or fluoro) and related alkyl derivatives containing a saturated or unsaturated alkyl group at the 5-position, thymine, uracil or 6-azapyrimidine, wherein the alkyl sidechain attached to the heterocyclic ring is a 2-hydroxymethylcyclopropylidenemethane moiety. The $R_1$, $R_2$ in Formulas 3 and 4 are alkyl or aryl groups, X is O and $R_1X$ and $R_2X$ can also be amino acid residues with X as NH.

The preferred compounds of the present invention are syn-$N^9$-(2-hydroxy-methylcyclopropylidenemethyl)adenine (synadenol), wherein in Formula 1, B is adenin-$N^9$-yl, syn-$N^9$-(2-hydroxymethylcyclopropylidenemethyl)guanine (synguanol), wherein B is guanin-$N^9$-yl, syn-$N^1$-(2-hydroxymethylcyclopropylidenemethyl)cytosine (syncytol) wherein in Formula 1, B is cytosin-$N^1$-yl, syn-2,6-diamino-$N^9$-(2-hydroxymethylcyclopropylidenemethyl)purine wherein in Formula 1, B is 2,6-diaminopurine, syn-2-amino-6-cyclopropylamino-$N^9$-(2-hydroxymethylcyclopropylidenemethyl)purine wherein in Formula 1, B is 2-amino-6-cyclopropylaminopurin-$N^9$-yl, syn-2-amino-6-chloro-$N^9$-(2-hydroxymethylcyclopropylidenemethyl)purine wherein in Formula 1 B is 2-amino-6-chloropurin-$N^9$-yl, syn-2-amino-6-methoxy-$N^9$-(2-hydroxymethylcyclopropylidenemethyl) purine wherein in Formula 1, B is 2-amino-6-methoxypurin-$N^9$-yl and syn-2-amino-6-azido-$N^9$-(2-hydroxymethylcyclopropylidenemethyl)purine wherein in Formula 1, B is 2-amino-6-azidopurin-$N^9$-yl.

The preferred compounds of the present invention are also methyl phenyl-phosphoro-L-alaninate of syn-$N^9$-(2-hydroxymethylcyclopropylidenemethyl)adenine (3, B=adenin-$N^9$-yl) and anti-$N^9$-(2-hydroxymethylcyclopropylidenemethyl)adenine (4, B is adenin-$N^9$-yl).

The nomenclature of the compounds of the present invention follows standard conventions. The numbering of the cyclopropylidenemethane moiety attached to the heterocyclic ring B is shown in Formulas 1 and 2. The purine and pyrimidine rings are numbered as indicated below:

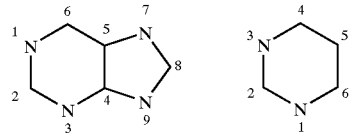

It is appreciated that heterocyclic rings containing hydroxy and amino groups are tautomeric with the corresponding oxo and imino compounds.

Preferred compounds of the present invention also include the R- and S-enantiomers of the compounds of Formulas 1 through 4. The compounds described by Formulas 1 through 4 contain an asymmetric carbon atom marked in the Formulas 1 and 2 by an asterisk. Compounds of Formula 1 and 2 of the present invention are therefore racemic mixtures of two optical antipodes which may be resolved by conventional methods such as chromatography or fractional crystallization of suitable diastereoisomeric derivatives such as salts or esters with optically active acids (camphor 10-sulfonic acid, methoxyacetic acid, dibenzoyltartaric acid, 6-methoxy-2-naphthyl-2-propanoic acid, etc.), by an enantioselective enzymic synthesis of esters of one antipode such as acetates or butyrates or by an enantioselective enzymic hydrolysis of esters of compounds of Formulas 1 and 2 such as acetates or butyrates. The suitable enzymes include, but are not limited to, lipases such as lipase AK, lipase P30 or esterases such as pig liver esterase. Racemic compounds containing adenine moiety may also be resolved by the action of adenosine deaminase. Alternatively, the R- and S-enantiomers can be obtained by synthetic methods utilizing enantiomerically pure starting materials as described in Examples 20 through 25.

Compounds 3 and 4 derived from racemic analogues 1 and 2 are mixtures of four diastereoisomers provided that $R_1X$ is not the same as $R_2X$.

The syntheses of compounds of the present invention are summarized in FIGS. 1 to 7. Generally, alkyl cis- and trans-2-halo-2-halomethylcyclopropane 1-carboxylates can be used as suitable alkylating agents. Ethyl cis- and trans-2-chloro-2-chloromethylcyclopropane 1 carboxylates were previously described. Dyakonov, I. A., et al., *J. Gen. Chem. USSR* (English translation) 25:1435–1440 (1955). More reactive cis- and trans-2-bromo-2-bromomethylcyclopropane-1-carboxylates 6 and 7, which are the preferred reagents, were prepared as follows: addition of ethyl diazoacetate to 2,3-dibromopropene (5) in the presence of suitable catalyst, e.g., dirhodium tetraacetate (Doyle, M. P., et al., *J. Org. Chem.* 46:5094–5102 (1981)) and organic solvent such as dichloromethane, afforded a mixture (1.5:1) of ethyl cis- and trans-2-bromo-2-bromomethylcyclopropane 1-carboxylates (6 and 7) as described in FIG. 1. The resultant mixture is then used for alkylation of heterocycles B–H (8, B=purine or pyrimidine moiety) in the presence of an appropriate base, e.g., potassium carbonate or sodium hydride in an organic solvent, e.g., N,N-dimethylformamide, to give a mixture of cis- and trans-1-bromo-2-(carbethoxy)cyclopropylmethylpurines or -pyrimidines 9 and 10 in the ratio of 1.5:1 as described in FIG. 2.

Figure 2:
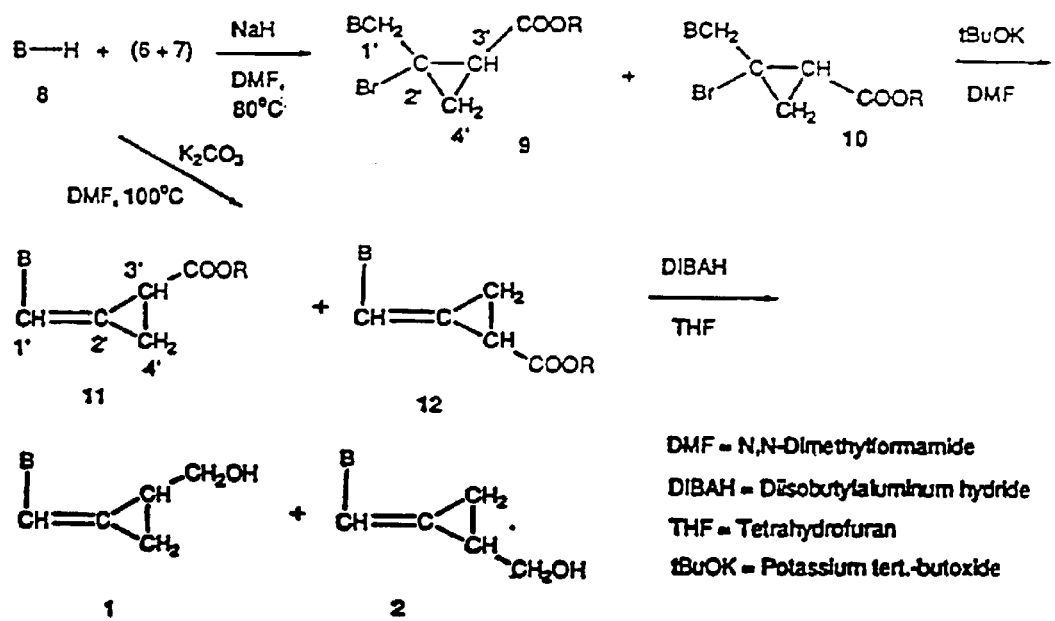
FIG. 2 shows the synthesis of purine and pyrimidine 2-hydroxymethyl-cyclopropylidenemethylpurines and -pyrimidines of Formulas 1 and 2.
Figure 3:
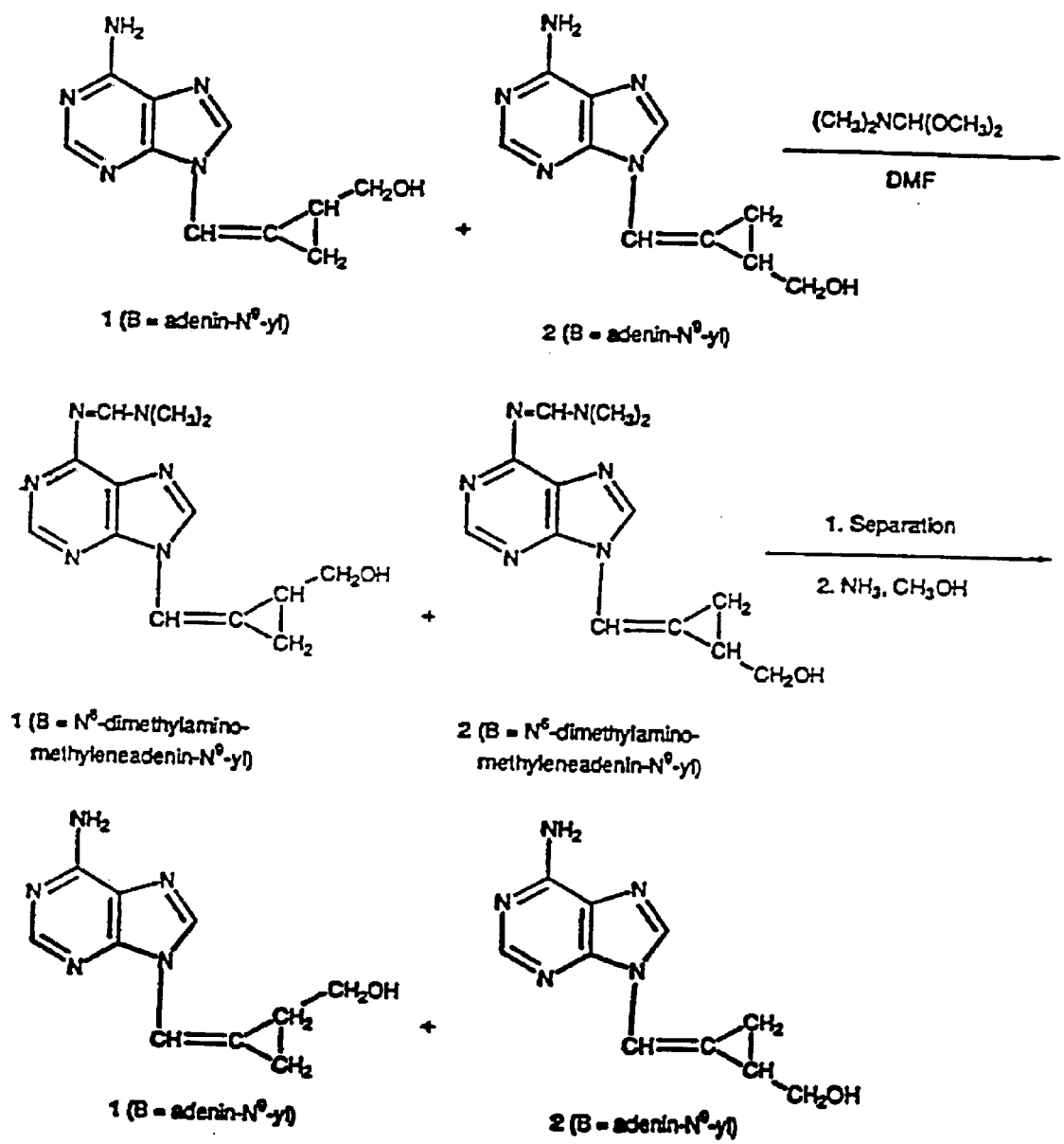
FIG. 3 shows the method for separation of syn-$N^9$-(2-hydroxymethyl-cyclopropylidenemethyl)adenine (1, B=adenin-$N^9$-yl) and anti-$N^9$-(2-hydroxymethyl-cyclopropylidenemethyl)adenine (2, B=adenin-$N^9$-yl)

A mixture of bromoesters 9 and 10 was converted to a mixture of syn- and anti-2-carbethoxycyclopropylidenemethylpurines or-pyrimidines 11 and 12 (R=$C_2H_5$) using a strong base, e.g., potassium tert.-butoxide in an appropriate solvent such as N,N-dimethylformamide as shown in FIG. 2.

Alternately, the alkylation and elimination can be combined into a single step. Thus, the reaction of heterocycle B–H (8, B=purine or pyrimidine moiety) with ethyl 2-bromo-2-bromomethylcyclopropane-1-carboxylates (6 and 7) is performed with potassium carbonate in N,N-dimethylformamide at an elevated temperature to give directly a mixture of the desired syn- and anti-2-carbethoxycyclopropylidenemethyl-purines or -pyrimidines 11 and 12 (R=$C_2H_5$) as shown in FIG. 2. A work up of the reaction mixture with methanol leads to transesterification to give methyl esters 11 and 12 (R=$CH_3$).

The reduction of carboethoxy or carbomethoxy group with a suitable reducing agent, e.g., diisobutylaluminum hydride and organic solvent such as tetrahydrofuran affords the compounds of the present invention, syn- and anti-2-hydroxymethylcyclo-propylidenemethylpurines or -pyrimidines 1 and 2, as described in FIG. 2. A mixture of compounds 1 and 2 is then separated by crystallization or chromatography on silica gel either directly or after a suitable derivatization.

For example, a mixture of syn- and anti-$N^9$-(2-hydroxymethylcyclopropylidene-methyl)adenines 1 and 2

(B=adenin-$N^9$-yl) is converted to the corresponding $N^6$-dimethylaminomethylene derivatives 1 and 2 (B=$N^6$-dimethylaminomethylene-adenin-$N^9$-yl) by reaction with N,N-dimethylformamide dimethyl acetal (Zemlicka, J., et al., *Collect. Czech. Chem. Commun.* 32:3159–3168 (1967)), in a suitable solvent such as N,N-dimethylformamide as described in FIG. 3. Compounds 1 and 2 (B=$N^6$-dimethylaminomethyleneadenin-$N^9$-yl) are then separated by chromatography on silica gel and each isomer is deprotected with ammonia in methanol to give compounds of the present invention, synadenol (1, B=adenin-$N^9$-yl) and anti isomer 2 (B=adenin-$N^9$-yl).

Syn- and anti-2-amino-6-chloro-$N^9$-(2-hydroxymethylcyclopropylidenemethyl)-purine 1 and 2 (B=2-amino-6-chloropurin-$N^9$-yl) are separated by column chromatography on silica gel. The syn and anti isomers 1 and 2 (B=2-amino-6-chloropurin-$N^9$-yl) are hydrolyzed with 80% formic acid (Harnden, M. R., et al., *J. Med. Chem.* 33:187–196 (1990)), to give compounds of the present invention, synguanol (1, B=guanin-$N^9$-yl) and anti isomer 2 (B=guanin-$N^9$-yl), as described in FIG. 4.

Figure 4:
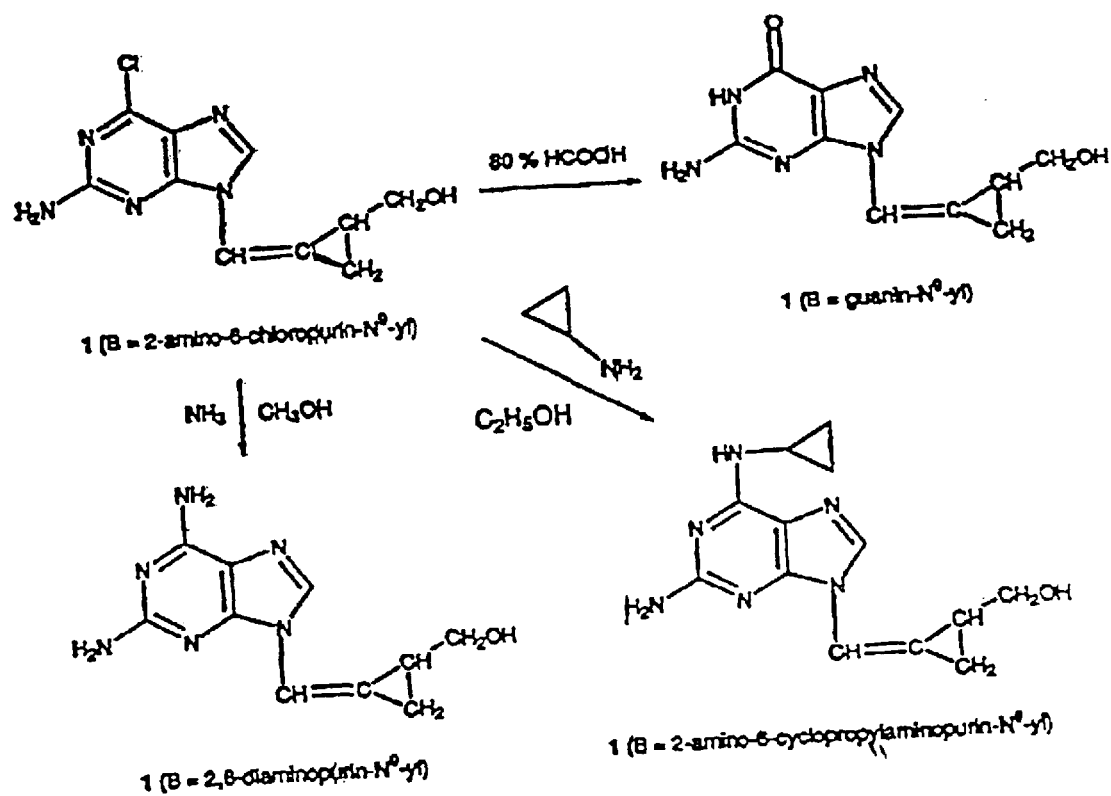
FIG. 4 shows the hydrolysis of syn-2-amino-6-chloro-$N^9$-(2-hydroxy-methylcyclopropylidenemethyl)purine (1, B=2-amino-6-chloropurine) and anti-2-amino-6-chloro-$N^9$-(2-hydroxymethylcyclopropylidenemethyl)purine (1, B=2-amino-6-chloropurine) to syn-$N^9$-(2-hydroxymethylcyclopropylidenemethyl)guanine (1, B=guanine) and anti-$N^9$-(2-hydroxymethylcyclo-propylidenemethyl)guanine (1, B=guanine).
Figure 5:
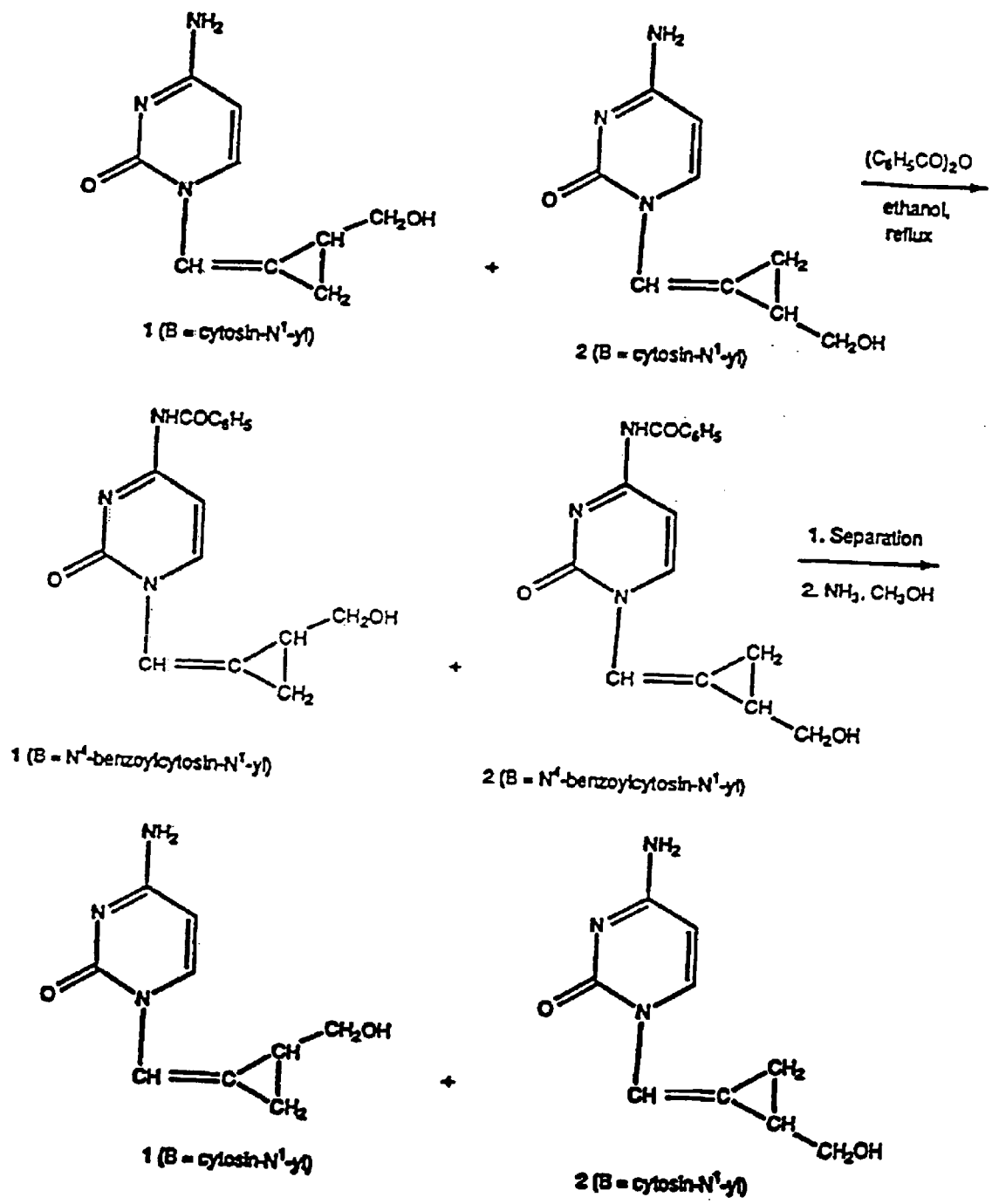
FIG. 5 shows the method for separation of syn-$N^1$-(2-hydroxymethyl-cyclopropylidenemethyl)cytosine (1, B=cytosin-$N^9$-yl) and trans-$N^1$-(2-hydroxy-methylcyclopropylidenemethyl)cytosine (2, B=cytosin-$N^1$-yl)

Ammonolysis of the syn-2-amino-6-chloro-$N^9$-(2-hydroxymethylcyclo-propylidenemethyl)purine 1 (B=2-amino-6-chloropurin-$N^9$-yl) affords syn-2,6-diamino-$N^9$-(2-hydroxymethylcyclopropylidenemethyl)purine 1 (B=2,6-diaminopurin-$N^9$-yl) as shown in FIG. 4.

Reaction of syn-2-amino-6-chloro-$N^9$-(2-hydroxymethylcyclopropylidene-methyl)purine 1 (B=2-amino-6-chloropurin-$N^9$-yl) with cyclopropylamine gives syn-2-amino-6-cyclopropylamino-$N^1$-(2-hydroxymethylcyclopropylidenemethyl)purine 1(B=2-amino-6-cyclopropylaminopurin-$N^9$-yl) as shown in FIG. 4.

The mixture of syn- and anti-$N^1$-(2-hydroxymethylcyclopropylidenemethyl)-cytosines 1 and 2 (B=cytosin-$N^1$-yl) is benzoylated with a suitable benzoylating agent such as benzoic anhydride in an appropriate solvent such as ethanol (Otter, B. A., et al., *N-Acyl Derivatives of 2'-Deoxycytidine in Synthetic Procedures in Nucleic Acid Chemistry*, Vol. 1, John Wiley & Sons, New York, pp. 285–287 (1967)) to give syn- and anti-($N^4$-benzoyl)-$N^1$-(2-hydroxymethylcyclopropylidenemethyl)cytosines 1 and 2 (B=$N^4$-benzoylcytosin-$N^1$-yl) which are separated by chromatography on silica gel as described in FIG. 5. The separated isomers are debenzoylated with ammonia in methanol to afford syn- and anti-$N^1$-(2-hydroxymethylcyclopropylidenemethyl)cytosine 1 and 2 (B=cytosin-$N^1$-yl).

Figure 6:
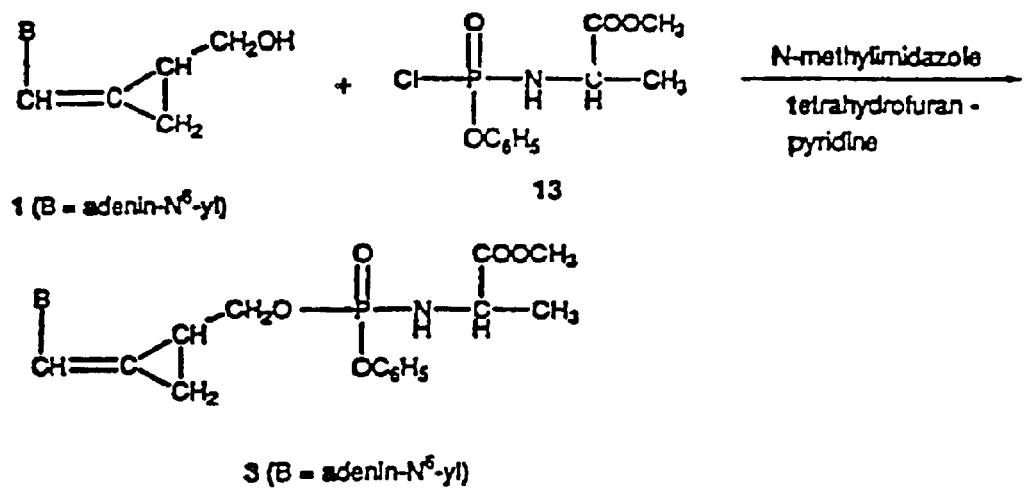
FIG. 6 shows the synthesis of methyl phenylphosphoro-L-alaninate of syn-$N^9$-(2-hydroxymethylcyclo-propylidenemethyl)adenine (3, B=adenin-$N^9$-yl)
Figure 7:
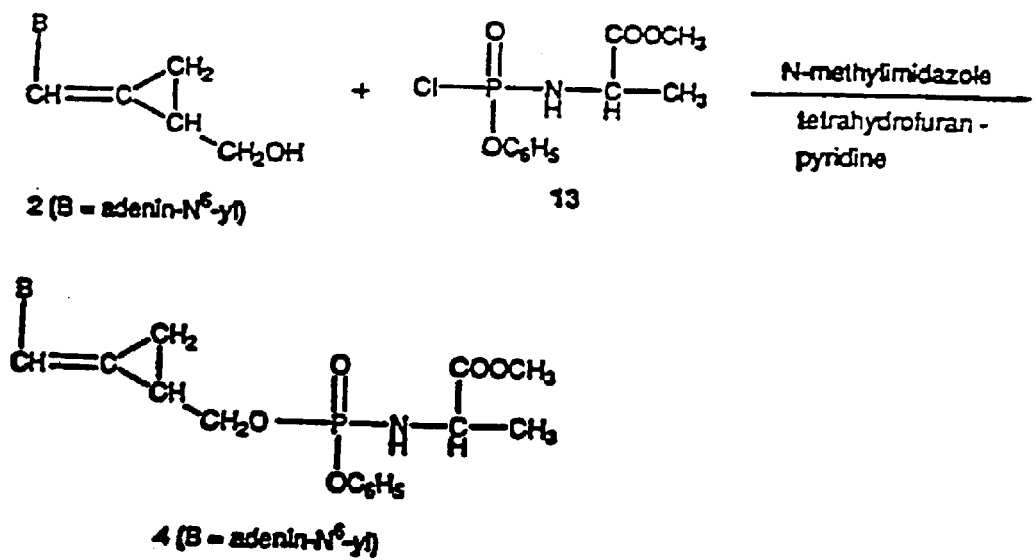
FIG. 7 shows the synthesis of methyl phenylphosphoro-L-alaninate of anti-$N^9$-(2-hydroxymethylcyclo-propylidenemethyl)adenine (4, B=adenin-$N^9$-yl).

Prodrugs of syn- and anti-$N^9$-(2-hydroxymethylcyclopropylidenemethyl)-adenines 3 and 4 (B=adenin-$N^9$-yl) were prepared by reaction of 1 and 2 (B=adenin-$N^9$-yl) with phenylmethoxyalaninylphosphorochloridate (13) (McGuigan, C., et al., *Antiviral Res.* 17:311–321 (1992)) using a suitable catalyst, e.g., N-methylimidazole, in an appropriate organic solvent such as tetrahydrofuran and pyridine as described in FIGS. 6 and 7.

The R- and S-enantiomers of the compounds of Formulas 1 through 4 can be synthesized utilizing (R)- and (S)-methylenecyclopranecarboxylic acids.

Compositions within the scope of invention include those comprising a novel compound of the present invention in an effective amount to achieve an intended purpose. Determination of an effective amount and intended purpose is within the skill of the art. Preferred dosages, which are dependent for example, on the severity of the infection and the individual patient's response to the treatment, can range from about 0.01 to about 100 mg/kg of body weight to give a blood concentration ranging from about 0.05 µg to about 5 mg per mL of whole blood.

As used herein, the term "pharmaceutically acceptable salts" is intended to mean salts of the compounds of the present invention with pharmaceutically acceptable acids, e.g., inorganic acids such as sulfuric, hydrochloric, phosphoric, etc. or organic acids such as acetic.

Pharmaceutically acceptable compositions of the present invention may also include suitable carriers comprising excipients and auxiliaries which facilitate processing of the active compounds into preparations which may be used pharmaceutically. Such preparations, preferably those which can be administered orally, include tablets, dragees and capsules. Further preferred preparations are those which can be administered rectally, such as suppositories, as well as suitable solutions for administration by injection or orally, contain from about 0.1 to about 99%, preferably about 25 to about 85%, of the active compound of the present invention, together with the excipient.

The pharmaceutical preparations of the present invention are manufactured in a manner which is itself known, e.g., using the conventional mixing, granulating, dragee-making, dissolving or lyophilizing processes. Thus, pharmaceutical preparations for oral use can be obtained by combining the active compounds with solid excipients, optionally grinding a resulting mixture and processing the mixture of granules, after adding suitable auxiliaries, if desired or necessary, to obtain tablets or dragee cores.

Suitable excipients are, in particular, fillers such as sugars, e.g., lactose or sucrose, mannitol or sorbitol, cellulose preparations and/or calcium phosphates, e.g., tricalcium diphosphate or calcium hydrogen phosphate, as well as binders such as starch paste, using, e.g., maize starch, wheat starch, rice starch, potato starch, gelatin, gum tragacanth, methyl cellulose and/or polyvinylpyrrolidone. If desired, disintegrating agents may be added such as the above-mentioned starches and also carboxymethyl starch, cross-linked polyvinylpyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated sugar solutions may be used, which may optionally contain gum arabic, talc, polyvinylpyrrolidone, polyethylene glycol and/or titanium dioxide, lacquer solutions and suitable organic solvent or solvent mixtures. In order to produce coatings resistant to gastric juices, solutions of suitable cellulose preparations, such as acetylcellulose phthalate or hydroxypropylmethylcellulose phthalate, are used. Dyestuffs or pigments may be added to the tablets or dragee coatings, e.g., for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules may contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be used.

Possible pharmaceutical preparations which can be used rectally include, e.g., suppositories, which consist of a combination of the active compounds with a suppository base. Suitable suppository bases are, e.g., natural or synthetic triglycerides, paraffin hydrocarbons, polyethylene glycols or higher alkanols. It is also possible to use gelatin rectal capsules which consist of a combination of the active compounds with a base. Possible base materials include, e.g., liquid triglycerides, polyethylene glycols or paraffin hydrocarbons.

Suitable formulations for parenteral administration include aqueous solutions of the active compounds in water-soluble form, e.g., water-soluble salts. In addition, suspension of the active compounds as appropriate oily injection suspensions may be administered. Suitable lipophilic solvents or vehicles include fatty oils, such as sesame oil, or synthetic fatty acid esters, e.g., ethyl oleate or triglycerides. Aqueous injection suspensions may contain substances which increase the viscosity of the suspension such as sodium carboxymethylcellulose, sorbitol and/or dextran. Optionally, the suspension may also contain stabilizers.

Alternatively, the active compounds of the present invention may be administered in the form of liposomes, pharmaceutical compositions wherein the active compound is contained either dispersed or variously present in corpuscles consisting of aqueous concentrate layers adherent to hydrophobic lipidic layer. The active compound may be present both in the aqueous layer and in the lipidic layer or in the non-homogeneous system generally known as a lipophilic suspension.

It will be appreciated that the active compounds of the present invention may be administered in combination with known antiviral agents, e.g., acyclovir, ganciclovir, zidovudine, AZT, ddl, ddC, 3TC and d4T.

The following Examples further describe the compounds of the present invention and the synthesis schemes for producing same.

EXAMPLE 1

Synthesis of cis and trans Ethyl 2-Bromo-2-bromomethylcyclopropane-1-carboxylates (6 and 7)

Ethyl diazoacetate (90% in dichloromethane, 23.3 mL, 0.20 mol) was added into a solution of dirhodium tetraacetate (22.1 mg, 0.05 mmol) in 2,3-dibromopropene (5, 97%, 68.0 g, 0.34 mol) and $CH_2Cl_2$ (3 mL) with the aid of a syringe pump at a rate of 1.1 mL/hour with stirring at room temperature. The reaction mixture was distilled in vacuo and the distillate was trapped at −78° C. to recover unreacted 2,3-dibromopropene (20 g, 29%). Water (100 mL) was added to the oily residue followed by a portionwise addition of powdered potassium permanganate at 0° C. with stirring. A total of 30 g of permanganate was consumed. The excess of permanganate was removed by addition of solid sodium thiosulfate. The mixture was filtered using a Celite pad and the solids were washed with ether (4×80 mL) with the aid of a sonicator. The filtrate was extracted with ether (4×70 mL). The combined ether portions were washed with saturated aqueous sodium bicarbonate (2×100 mL), water (2×250 mL) and brine (2×100 mL). After drying with sodium sulfate and evaporation of ether a mixture of products 6 and 7 was obtained as a yellow oil (51.9 g, 91% yield), $n_D^{25}$=1.5131. It was of sufficient purity to be used in the subsequent steps (Examples 2, 4, 6 and 10). The $^1H$ NMR spectrum indicated a mixture of cis and trans isomers 6 and 7 in the ratio of 1.5:1. Distillation of a sample of this product (5.0 g) gave colorless liquid (4.5 g), bp. 59–64° C./0.25 mmHg, $n_D^{25}$= 1.5139.

IR (neat): 1733 $cm^{-1}$ (C=O, ester), 1036 and 868 $cm^{-1}$ (cyclopropane ring).

$^1H$ NMR ($CDCl_3$) ∂, cis isomer 1.30 (t, 3, $CH_3$), 1.73 (t, 1) and 1.85 (dd, 1, $H_3$), 2.47 (dd, 1, $H_2$), 3.97 (d, 2, $CH_2Br$), 4.19 (q, 2, $OCH_2$); trans isomer 1.29 (t, 3, $CH_3$), 1.52 (dd, 1) and 1.89 (t, 1, $H_3$), 2.10 (dd, 1, $H_2$), 3.76 (d, 2, $CH_2Br$), 4.21 (q, 2, $OCH_2$).

$^{13}C$ NMR ($CDCl_3$) ppm, cis isomer 14.14 ($CH_3$), 26.43 ($C_3$), 31.44 ($C_1$), 37.21 ($C_2$), 38.91 ($CH_2Br$), 61.66 ($OCH_2$), 169.32 (C=O); trans isomer 14.30 ($CH_3$), 22.34 ($C_3$), 29.01 ($C_1$), 35.86 ($C_2$), 42.02 ($CH_2Br$), 61.59 ($OCH_2$), 168.12 (C=O).

EI-MS 288 (M, 0.3), 286 (M, 1.9) and 284 (M, 0.5), 256 (1.6), 258 (2.6) and 260 (1.2), 243 (5.0), 241 (10.2) and 239 (5.3), 211 (7.0), 213 (13.8) and 215 (7.4), 205 (52.2) and 207 (51.0), 177 (96.7) and 179 (94.4), 159 (7.1) and 161 (7.0), 131 (15.2) and 133 (16.8), 97 (30.4), 81 (15.3), 69 (16.3), 53 (70.8), 39 (15.9), 28 (CO, 100.0);

HRMS: Calculated for $C_7H_{10}{}^{79}Br_2O_2$: M 283.90475. Found: M 283.9048.

Calculated for $C_7H_{10}Br_2O_2$: C, 29.59; H, 3.55; Br, 55.59. Found: C, 29.61; H, 3.62; Br, 55.37.

EXAMPLE 2

Synthesis of cis-$N^9$-(1-Bromo-2-carbethoxycyclopropylmethyl)adenine and trans-$N^9$-(1-Bromo-2-carbethoxycyclopropylmethyl)adenine 9 and 10.

A mixture of dibromoesters 6 and 7 (858 mg, 3.0 mmol) from Example 1 was added into a suspension of sodium salt of adenine which was prepared from adenine (405 mg, 3.0 mmol) and sodium hydride (60% dispersion in mineral oil, 120 mg, 3.0 mmol) in N,N-dimethylformamide (25 mL) with stirring under nitrogen at room temperature. The resultant mixture was heated to 80° C. (bath temperature) for 12 hours. The solvent was evaporated in vacuo (oil pump), the residue was adsorbed on silica gel (3 g) which was then put on the top of a silica gel (70 g) column. The elution was performed with dichloromethane—methanol (96:4 and 94:6) the cis isomer 9(305 mg, 29.9% yield) and trans isomer 10 (180 mg, 17.6% yield) were obtained as pale yellow solids. Analytical samples were obtained by recrystallization from benzene—ethyl acetate (cis isomer 9) and benzene (trans isomer 10).

Cis isomer 9:
Mp. 200–203° C.
UV (ethanol) max 260 nm (ϵ 14,900), 209 nm (ϵ19,500).
IR (KBr) 3340 and 3150 $cm^{-1}$ ($NH_2$), 1725 $cm^{-1}$ (C=O, ester), 1670, 1600 and 1580 $cm^{-1}$(adenine ring), 1045, 1015 and 867 $cm^{-1}$ (cyclopropane ring).
$^1H$ NMR ($CD_3SOCD_3$)∂ 1.23 (t, 3, $CH_3$), 1.76 (dd, 1) and 2.00 (t, 1, $H_{4'}$), 2.49 (dd, 1, $H_3$,of cyclopropane), 4.18 (q, 2, $OCH_2$), 4.66 (s, 2, $H_{1'}$), 7.24 (s, 2, $NH_2$), 8.10 (s, 2, $H_2$ and $H_8$ of adenine).
$^{13}C$ NMR ($CD_3SOCD_3$) ppm 13.52 ($CH_3$), 22.25 ($C_{4'}$), 28.57 ($C_{3'}$), 36.28 ($C_{2''}$), 46.64 ($C_{1'}$), 60.75 ($OCH_2$), 168.82 (C=O); adenine ring: 118.10 ($C_5$), 140.46 ($C_8$), 149.20 ($C_4$), 152.03 ($C_2$), 155.49 ($C_6$).
FAB-MS (thioglycerol matrix) 341 and 343 (M+2H, 20.3, 18.6), 340 and 342 (M+H, 98.4, 100.0), 262 (8.0), 214 (4.3), 188 (5.9), 136 (25.2).

Calculated for $C_{12}H_{14}BrN_5O_2$: C, 42.47; H, 4.16; Br, 23.28; N, 20.65. Found: C, 42.24; H, 4.29; Br, 23.15; N, 20.59.

Trans isomer 10:

Mp. 186–189° C.

UV (ethanol) max 260 nm ($\epsilon$ 14,700), 209 nm ($\epsilon$ 18,700).

IR (KBr) 3350 and 3160 cm$^{-1}$ (NH$_2$), 1745 cm$^{-1}$ (C=O, ester), 1655, 1605 and 1585 cm$^{-1}$ (adenine ring), 1045, 1015 and 865 cm$^{-1}$ (cyclopropane ring).

$^1$H NMR (CDCl$_3$)$\partial$ 1.14 (t, 3, CH$_3$), 1.57 (t, 1) and 1.93 (dd, 1, H$_{4'}$), 2.64 (dd, 1, H$_{3'}$), 4.07 (q, 2, OCH$_2$), 4.52 (d, 2, H$_{1'}$), 7.27 (s, 2, NH$_2$), 8.13 and 8.17 (2s, 2, H$_2$ and H$_8$ of adenine).

$^{13}$C NMR (CDCl$_3$) ppm 13.70 (CH$_3$), 19.95 (C$_{4'}$), 26.05 (C$_{3'}$), 36.99 (C$_{2'}$), 51.93 (C$_{1'}$), 60.42 (OCH$_2$), 167.63 (C=O); adenine ring: 118.01 (C$_5$), 140.30 (C$_8$), 149.23 (C$_4$), 152.14 (C$_2$), 155.55 (C$_6$).

FAB-MS (thioglycerol matrix) 341 and 343 (M+2H, 19.0, 18.2), 340 and 342 (M+H, 96.3, 100.0), 262 (32.1), 214 (12.1), 188 (12.5), 136 (78.3).

Calculated for $C_{12}H_{14}BrN_5O_2$: C, 42.47; H, 4.16; Br, 23.28; N, 20.65. Found: C, 42.60; H, 4.34; Br, 23.14; N, 20.87.

EXAMPLE 3

Synthesis of syn-$N^9$-(2-Carbethoxycyclopropylidenemethyl)adenine (11, B=adenin-$N^9$-yl, R=ethyl) and anti-$N^9$-(2-Carbethoxycyclo-propylidenemethyl)adenine (12, B=adenin-$N^9$-yl, R=ethyl) Using Bromoesters 9 and 10 as Starting Materials.

Solid potassium tert.-butoxide (505 mg, 4.5 mmol) was added into a solution of bromoesters 9 and 10 from Example 2 (1.02 g, 1.023 mmol) in DMF (35 mL) at 0° C. with stirring under nitrogen. The stirring continued for 2 hours. The reaction mixture was then added dropwise into saturated aqueous ammonium chloride (20 mL) at 0° C. with stirring. After 15 minutes, the solvents were removed by evaporation in vacuo at room temperature. The residue was chromatographed on a silica gel column using dichloromethane-methanol (9:1) as an eluent to give the mixture of compounds 11 and 12 (B=adenine-$N^9$-yl, R=ethyl, 545 mg, 70% yield) as a white powder. Mp. 166–175° C. after recrystallization from benzene. The $^1$H NMR indicated the presence of syn and anti isomers 10 and 11 (B=adenin-$N^9$-yl, R=ethyl) in the ratio of 1.5:1.

UV (ethanol) max 276 nm (shoulder, $\epsilon$ 7,600), 256 nm (shoulder, $\epsilon$ 11,800), 228 nm ($\epsilon$ 22,500).

IR (KBr) 3350 and 3160 cm$^1$ (NH$_2$), 1735 cm$^{-1}$ (C=O, ester), 1660, 1605 and 1585 cm$^{-1}$ (adenine ring and olefin).

$^1$H NMR (CD$_3$SOCD$_3$) $\partial$, syn isomer 11 (B=adenine-$N^9$-yl, R=ethyl) 1.13 (t, 3, CH$_3$), 1.91 (ddd, 1) and 2.00 (t d, 1, H$_{4'}$), 2.89 (ddd, 1, H$_{3'}$), 4.02–4.13 (m, 2, OCH$_2$), 7.40 (s, 2, NH$_2$), 7.54 (q, 1, H$_{1'}$), 8.15 (s, 1) and 8.23 (s, 1, H$_2$ and H$_8$ of adenine); anti isomer 12 (B=adenine-$N^9$-yl, R=ethyl) 1.19 (t, 3, CH$_3$), 2.07 (ddd, 1) and 2.17 (t d, 1, H$_{4'}$), 2.64 (ddd, 1, H$_{3'}$), 4.02–4.13 (m, 2, OCH$_2$), 7.39 (s, 2, NH$_2$), 7.59 (q, 1H, H$_{1\alpha}$), 8.18 (s, 1, H$_2$ of adenine), 8.52 (s, 1, H$_8$ of adenine).

13C NMR (CD$_3$SOCD$_3$) ppm, syn isomer 11 (B=adenine-$N^9$-yl, R=ethyl) 10.70 (C$_{4'}$), 14.52 (CH$_3$), 19.78 (C-3'), 61.10 (OCH$_2$), 111.71 (C$_{1'}$), 112.85 (C$_{2'}$), 170.71 (C=O); adenine ring: 118.90 (C$_5$), 137.75 (C$_8$), 148.76 (C$_4$), 153.64 (C$_2$), 156.56 (C$_6$); anti isomer 12 (B=adenine-$N^9$-yl, R=ethyl) 13.30 (C$_{4'}$), 14.52 (CH$_3$), 17.52 (C$_{3'}$), 61.10 (OCH$_2$), 112.18 (C$_{1'}$), 113.16 (C$_{2'}$), 171.29 (C=O); adenine ring: 118.90 (C$_5$), 137.99 (C$_8$), 148.76 (C$_4$), 153.64 (C$_2$), 156.56 (C$_6$).

EI-MS 259 (M, 54.2), 245 (6.1), 230 (24.3), 214 (28.4), 202 (M, 9.9), 187 (100.0), 160 (19.6), 135 (22.4).

Calculated for $C_{12}H_{13}N_5O_2$: C, 55.58; H, 5.06; N, 27.02%. Found: C, 55.60; H, 4.82; N, 27.28%.

EXAMPLE 4

Direct Synthesis of syn-$N^9$-(2-Carbethoxycyclopropylidenemethyl)adenine (11, B=adenin-$N^9$-yl, R=ethyl) and anti-$N^9$-(2-Carbethoxycyclopropylidenemethyl)adenine (12, B=adenin-$N^9$-yl, R=ethyl) from Adenine.

A mixture of adenine (810 mg, 6.0 mmol), cis- and trans ethyl 2-bromo-2-bromomethylcyclopropane 1-carboxylates (6 and 7, 2.14 g, 7.5 mmol) from Example 1 and flame-dried potassium carbonate (4.98 g, 36.0 mmol) in N,N-dimethylformamide (30 mL) was stirred at 100° C. under nitrogen for 22 hours. After cooling, the insoluble portion was filtered off and it was washed with a mixture of dichloromethane—ethanol (4:1, 2×50 mL). The filtrate was evaporated and the residue was flash-chromatographed on a silica gel column with dichloromethane—methanol (95:5) as an eluent. Evaporation of appropriate fractions gave a mixture of products 11 and 12 (B=adenin-$N^9$-yl, R=ethyl) as a pale yellow solid (610 mg, 39.2% yield), mp. 166–175° C. in the ratio of 2:1 as determined by $^1$H NMR.

EXAMPLE 5

Synthesis of Synadenol (1, B=adenin-$N^9$-yl) and anti-$N^9$-(2-Hydroxymethylcyclopropylidenemethyl) adenine (2, B=adenin-$N^9$-yl).

Diisobutylaluminum hydride in tetrahydrofuran (1 M, 27.2 mL, 27.2 mmol) was added dropwise into a solution of esters 11 and 12 (B=adenin-$N^9$-yl, R=ethyl, 881 mg, 3.4 mmol) from Example 3 or 4 in tetrahydrofuran (50 mL) at 0° C. over 10 minutes with stirring under nitrogen. The stirring at 0° C. was continued for 3.5 hours. Saturated aqueous ammonium chloride (25 mL) was then added with stirring at 0° C. The gel-like solid was filtered off using a Celite bed and it was washed with dichloromethane—methanol (1:1, 5×40 mL). The combined filtrate and washings were evaporated and the residue was chromatographed on a silica gel column using dichloromethane—methanol (9:1 and 85:15) as eluents. The appropriate fractions were evaporated to give a mixture of compounds 1 and 2 (B=adenin-$N^9$-yl) as a pale yellow solid (557 mg, 75% yield).

A solution of this mixture of products (557 mg, 2.56 mmol) in N,N-dimethylformamide (30 mL) and N,N-dimethylformamide dimethyl acetal (0.51 mL, 3.85 mmol) was stirred at room temperature for 14 hours. Evaporation of the volatile components in vacuo at room temperature (oil pump) left a mixture of compound 1 and 2 (B=$N^6$-dimethylaminomethyleneadenin-$N^9$-yl) as a viscous yellow sirup which was flash-chromatographed on a silica gel column using dichloromethane-methanol (92:8 and 85:15). The appropriate fractions were pooled and evaporated to give syn isomer 1 (B=$N^6$-dimethylaminomethyleneadenin-$N^9$-yl), 264 mg, 37.8% yield) as a white solid and anti isomer 2 (B=$N^6$-dimethylaminomethyleneadenin-$N^9$-yl, 260 mg, 37.2% yield) as a foam. A small portion of 1 and 2 (B=$N^6$-dimethylaminomethyleneadenin-$N^9$-yl, 63 mg, 9.0% yield) was recovered as a mixture. Syn isomer 1 (B=$N^6$-dimethylaminomethyleneadenin-$N^9$-yl):

Mp. 172–178° C.

UV (ethanol) max 311 nm ($\epsilon$ 31,300), 233 nm ($\epsilon$ 27,600).

IR (KBr) 3500–3180 cm$^{-1}$ (OH), 1638 and 1600–1540 cm$^{-1}$ (olefin and $N^6$-dimethylaminomethyleneadenine), 1060, 1030, 830 and 810 cm$^{-1}$ (cyclopropane ring).

$^1$H NMR (CD$_3$SOCD$_3$) $\partial$ 1.21 (t, 1) and 1.49 (t, 1, H$_{4'}$), 2.14 (dq, 1, H$_{3'}$), 3.17 and 3.10/2s, 6, N(CH$_3$)$_2$/, 3.29 (t, overlapped with H$_2$O, 1) and 3.74 (dt, 1, H$_{5'}$), 5.11 (t, 1, OH), 7.43 (s, 1, H$_{1'}$), 8.42 (s, 1, H$_2$ of purine), 8.86 (s, 1, H$_8$ of purine), 8.90/s, 1, N=CHN(CH$_3$)$_2$/.

$^{13}$C NMR (CD$_3$SOCD$_3$) ppm 6.74 (C$_{4'}$), 19.73 (C$_{3'}$), 35.00 and 41.13/N(CH$_3$)$_2$/, 63.38 (C$_{5'}$), 110.60 (C$_{1'}$), 116.18 (C$_{2'}$), 152.77/N=CHN(CH$_3$)$_2$/; purine ring: 125.38 (C$_5$), 139.98 (C$_8$), 150.40 (C$_4$), 158.53 (C$_2$), 159.66 (C$_6$).

FAB-MS (thioglycerol matrix) 381 (M+thioglycerol+H, 5.7), 273 (M+H, 7.4), 191 (8.2), 149 (29.8), 91 (100.0). Anti isomer 2 (B=$N^6$-dimethylaminomethyleneadenin-$N^9$-yl):

UV (ethanol) max 310 nm ($\epsilon$ 32,300), 231 nm ($\epsilon$ 29,500).

IR (KBr) 3550–3200 cm$^{-1}$(OH), 1635 and 1600–1540 cm$^{-1}$(olefin and $N^6$-dimethylaminomethyleneadenine), 1030 and 810 cm$^{-1}$ (cyclopropane ring).

$^1$H NMR (CD$_3$SOCD$_3$) $\delta$ 1.39 (ddd, 1) and 1.71 (td, 1, H$_{4'}$), 1.97 (dqd, 1, H$_{3'}$), 3.17 and 3.11/2s, 6, N(CH$_3$)$_2$/, 3.41 (t, 2, H$_5$), 4.82 (t, 1, OH), 7.52 (d, 1, H$_{1'}$), 8.43 (s, 1H, H$_2$ of purine), 8.56 (s, 1, H$_8$ of purine), 8.89/s, 1, N=CHN(CH$_3$)$_2$/.

$^{13}$C NMR (CD$_3$SOCD$_3$) ppm 7.93 (H$_{4'}$), 18.09 (H$_{3'}$), 35.04 and 41.14 IN(CH$_3$)$_2$/, 63.57 (C$_{5'}$), 110.74 (C$_{1'}$), 116.59 (C$_{2'}$), 152.80/N=CHN(CH$_3$)/, purine ring: 125.40 (C$_5$), 139.47 (C$_8$), 150.59 (C$_4$), 158.48 (C$_2$), 159.67 (C$_6$).

FAB-MS (thioglycerol matrix) 381 (M+thioglycerol+H, 51.7), 273 (M+H, 100.0), 191 (69.8).

The separated isomers (250 mg, 0.92 mmol of each) were dissolved in methanolic ammonia saturated at 0° C. (100 mL). The mixtures were stirred at room temperature for 16 hours. The volatile components were evaporated and the residues were recrystallized from methanol to give synadenol (1, B=adenin-$N^9$-yl, 170 mg, 85% yield) and the anti isomer 2 (B=adenin-$N^9$-yl, 172 mg, 86% yield). Synadenol 1 (B=adenin-$N^9$-yl):

Mp. 238–239° C. (change of modification at 200–231° C.).

UV (ethanol) max 276 nm (shoulder, $\epsilon$ 9,300), 261 nm ($\epsilon$ 13,500), 226 nm ($\epsilon$ 29,400).

IR (KBr): 3300 and 3100 cm$^{-1}$ (NH$_2$ and OH), 1670, 1600 and 1580 cm$^{-1}$ (adenine ring and olefin), 1047 and 1025 cm$^{-1}$ (cyclopropane ring).

$_1$H NMR (CD$_3$SOCD$_3$) $\delta$ 1.22 (m, 1) and 1.50 (dt, 1, H$_{4'}$), 2.48 (m, 1, H$_{3'}$), 3.33 (m, overlapped with H$_2$O) and 3.73 (qt, 1, H$_{5'}$), 5.11 (t, 1, OH), 7.33 (s, 2, NH$_2$), 7.48 (d, 1, H$_{1'}$), 8.17 (s, 1, H$_2$ of adenine), 8.74 (s, 1, H$_8$ of adenine).

$^{13}$C NMR (CD$_3$SOCD$_3$) ppm 6.72 (C$_{4'}$), 19.70 (C$_{3'}$), 63.35 (C$_{5'}$), 110.69 (C$_{1'}$), 115.87 (C$_{2'}$); adenine ring: 118.84 (C$_5$), 138.13 (C$_8$), 148.13 (C$_4$), 153.42 (C$_2$), 156.47 (C$_6$).

EI-MS 217 (M, 31.4), 200 (45.2), 187 (37.0), 173 (6.5), 159 (11.2), 148 (15.3), 135 (100.0).

HRMS: Calculated for C$_{10}$H$_{11}$N$_5$O: M, 217.0964. Found: M, 217.0960.

Calculated for C$_{10}$H$_{11}$N$_5$O: C, 55.29; H, 5.10; N, 32.24. Found: 55.32; H, 4.99; N, 32.44.

Anti isomer 2 (B=adenin-$N^9$-yl):

Mp. 208–210° C.

UV (ethanol) max 277 nm (shoulder, $\epsilon$ 8,900), 261 nm ($\epsilon$ 12,200), 226 nm ($\epsilon$ 27,600).

IR (KBr) 3340 and 3180 cm$^1$ (NH$_2$ and OH), 1666, 1612, and 1578 cm$^{-1}$ (adenine ring and olefin).

$^1$H NMR (CD$_3$SOCD$_3$) a 1.38 (m, 1) and 1.71 (dt, 1, H$_{4'}$), 1.97 (dqt, 1, H$_{3'}$), 3.41 (t, 2, H$_{5'}$), 4.82 (t, 1, OH), 7.34 (s, 2, NH$_2$), 7.48 (q, 1, H$_{1'}$), 8.17 (s, 1, H$_2$ of adenine), 8.48 (s, 1, H$_8$ of adenine).

$^{13}$C NMR (CD$_3$SOCD$_3$) ppm 9.68 (C$_{4'}$), 18.06 (C$_{3'}$), 63.59 (C$_{5'}$), 110.81 (C$_{1'}$), 116.24 (C$_{2'}$); adenine ring: 118.85 (C$_5$), 137.61 (C$_8$), 148.68 (C$_4$), 153.48 (C$_2$), 156.49 (C$_6$).

EI-MS 217 (M, 15.0), 200 (78.5), 172 (25.9), 148 (11.3), 136 (43.1), 41 (100.0).

HRMS: Calculated for C$_{10}$H$_{11}$N$_5$O: M 217.0964; Found: M 217.0954.

Calculated for C$_{10}$H$_{11}$N$_5$O: C, 55.29; H, 5.10; N, 32.24. Found: C, 55.41; H, 5.20; N, 32.26.

EXAMPLE 6

Synthesis of syn-2-Amino-6-chloro-$N^9$-(2-carbethoxycyclopropylidenemethyl)purine (11, B=2-amino-6-chloropurin-$N^9$-yl, R=ethyl) and anti-2-Amino-6-chloro-$N^9$-(2-carbethoxycyclopropylidenemethyl)purine (12, B= 2-amino-chloropurin-$N^9$-yl, R=ethyl) from 2-Amino-6-chloropurine.

A mixture of 2-amino-6-chloropurine (8, B=2-amino-6-chloropurin-$N^9$-yl, 2.04 g, 12 mmol), dibromoesters 6+7 (5.29 g, 15 mmol) from Example 1 and flame-dried potassium carbonate (8.29 g, 60 mmol) in N,N-dimethylformamide (60 mL) was stirred at 100° C. (bath temperature) for 20 hours under nitrogen. Chromatography on a silica gel column (80 g) using dichloromethane—methanol (98.5:1.5 and 97:3) gave a crude mixture of esters 11 and 12 (B=2-amino-6-chloropurin-$N^9$-yl, R=ethyl, 1.98 g, 56.2% yield) in the ratio of 2:1 as indicated by $^1$H NMR as a yellow solid.

Mp. 177–196° C. after recrystallization from benzene or 171–187° C. after recrystallization from ethanol.

UV (ethanol) max 311 nm ($\epsilon$ 7,400), 230 nm ($\epsilon$ 26,800), 210 nm (shoulder, $\epsilon$ 16,100).

IR (KBr) 3420,3325 and 3220 cm$^{-1}$ (NH$_2$), 1725 cm$^{-1}$ (C=O, ester), 1646, 1615 and 1565 cm$^{-1}$ (purine ring and olefin), 1000 cm$^{-1}$ (cyclopropane ring).

$^1$H NMR (CD$_3$SOCD$_3$) $\delta$, syn isomer 11 (B=2-amino-6-chloropurin-$N^9$-yl, R=ethyl) 1.10 (t, 3, CH$_3$), 1.91 (ddd, 1) and 2.00 (td, 1, H$_{4'}$), 2.90 (ddd, 1, H$_{3'}$), 4.02–4.12 (m, 2, OCH$_2$), 6.99 (s, 2, NH$_2$), 7.35 (q, 1, H$_{1'}$), 8.19 (s, 1, H$_8$ of purine); anti isomer 12 (B=2-amino-6-chloropurin-$N^9$-yl, R=ethyl) 1.18 (t, 3, CH$_3$), 2.07 (ddd, 1) and 2.17 (ddd, 1, H$_{4'}$), 2.63 (ddd, 1, H$_{3'}$), 4.02–4.12 (m, 2, OCH$_2$), 7.04 (s, 2, NH$_2$), 7.42 (q, 1, H$_{1'}$), 8.46 (s, 1, H$_8$ of purine).

$^{13}$C NMR (CD$_3$SOCD$_3$) ppm, syn isomer 11 (B=2-amino-6-chloropurin-$N^9$-yl, R=ethyl) 10.75 (C$_{4'}$), 14.42 (CH$_3$), 19.76 (C$_{3'}$), 61.17 (OCH$_2$), 111.17 (C$_{1'}$), 113.74 (C$_{2'}$), 170.58 (C=O); purine ring: 123.49 (C$_5$), 139.75 (C$_8$), 150.27 (C$_4$), 152.95 (C$_2$), 160.55 (C$_6$); anti isomer 12 (B=2-amino-6-chloropurin-$N^9$-yl, R=ethyl) 13.45 (C$_{4'}$), 14.50 (CH$_3$), 17.67 (C$_{3'}$), 61.09 (OCH$_2$), 111.84 (C$_{1'}$), 114.11 (C$_{2'}$), 170.14 (C=O); purine ring: 123.57 (C$_5$), 140.23 (C$_8$), 150.19 (C$_4$), 153.10 (C$_2$), 160.55 (C$_6$).

EI-MS 293 and 295 (M 89.4, 29.9), 264 and 266 (30.8, 11.5), 248 and 250 (22.7, 8.7), 236 and 238 (10.9, 4.0), 221 and 223 (100.0, 32.9), 208 and 210 (5.9, 3.2), 184 (25.3), 169 and 171 (39.1, 14.1).

HRMS Calculated for $C_{12}H_{12}{}^{35}ClN_5O_2$: M 293.06795. Found: M 293.0680.

Calculated for $C_{12}H_{12}ClN_5O_2$: C, 49.14; H, 4.13; Cl, 11.93; N, 23.89. Found: C, 49.00; H, 4.27; Cl, 12.11; N, 24.18.

EXAMPLE 7

Synthesis of syn-2-Amino-6-chloro-$N^9$-(2-carbethoxycyclopropylidenemethyl)purine (1, B=2-amino-6-chloropurin-$N^1$-yl) and anti-2-Amino-6-chloro-$N^9$-(2-hydroxymethylcyclopropylidenemethyl)purine (1, B=2-amino-6-chloropurin-$N^9$-yl).

Diisobutylaluminum hydride in cyclohexane (1 M, 19.4 mL, 19.4 mmol) was added dropwise into a solution of esters 11 and 12 (B=2-amino-6-chloropurin-$N^9$-yl, R=ethyl, 1.90 g, 6.47 mmol) from Example 6 in tetrahydrofuran (100 mL) during 10 min. with stirring at 0° C. under nitrogen. Two additional portions of hydride (6.47 mL, 6.47 mmol) were added in 30 min. intervals. The stirring at 0° C. was continued for a total of 2 hours. The reaction was carefully quenched by adding aqueous methanol (50%, 10 mL) with stirring which was continued for 30 min. at 0° C. and then overnight at room temperature. The precipitated gel was filtered off and it was washed thoroughly with dichloromethane-methanol (4:1, 2×50 mL). The combined filtrate and washings were evaporated and the residue was chromatographed on a silica gel column using dichloromethane-methanol (97:3 and 92:8). The fractions of separated products 1 and 2 (B=2-amino-6-chloropurin-$N^9$-yl) were rechromatographed to give syn isomer 1 (B=2-amino-6-chloropurin-$N^9$-yl, 680 mg, 41.8% yield) and anti isomer 2 (B=2-amino-6-chloropurin-$N^9$-yl, 380 mg, 23.3% yield). Analytical samples of both isomers were obtained by recrystallization from ethanol.

Syn isomer 1 (B=2-amino-6-chloropurin-$N^9$-yl):
Mp. 214–216° C.
UV (ethanol) max 310 nm ($\epsilon$ 8,000), 233 nm ($\epsilon$ 31,800).
IR (KBr) 3440 (shoulder), 3330 and 3200 cm$^{-1}$ (OH and NH$_2$), 1640,1610 and 1570 cm$^{-1}$ (purine ring and olefin), 1040 and 1005 cm$^{-1}$ (cyclopropane ring).
$^1$H NMR (CD$_3$SOCD$_3$) δ 1.21 (ddd, 1) and 1.49 (td, 1, H$_{4'}$), 2.13 (dqd, 1, H$_{3'}$), 3.28 (ddd, overlapped with H$_2$O at 3.30, 1) and 3.73 (dt, 1, H$_{5'}$), 5.06 (dd, 1, OH), 7.01 (s, 2, NH$_2$), 7.20 (q, 1, H$_{1'}$), 8.70 (s, 1, H$_8$ of purine).
$^{13}$C NMR (CD$_3$SOCD$_3$) ppm 6.80 (C$_{4'}$), 19.73 (C$_{3'}$), 63.25 (C$_{5'}$), 110.24 (C$_{1'}$), 116.81 (C$_{2'}$); purine ring: 123.52 (C$_5$), 140.36 (C$_8$), 150.00 (C$_4$), 152.81 (C$_2$), 160.49 (C$_6$).
EI-MS 251 and 253 (M, 41.4, 15.1), 234 and 236 (50.9, 19.8), 221 and 223 (18.6, 8.9), 198 (26.2), 170 and 172 (100.0, 38.5).
Calculated for $C_{10}H_{10}ClN_5O$: C, 47.80; H, 4.01; Cl, 13.93; N, 27.89. Found: C, 47.70; H, 4.07; Cl, 14.18; N, 27.86.

Anti isomer 2 (B=2-amino-6-chloropurin-$N^9$-yl):
Mp 201–204° C.
UV (ethanol) max 310 nm ($\epsilon$8,100), 231 nm ($\epsilon$33,700).
IR (KBr) 3460, 3340 and 3220 cm$^{-1}$ (OH and NH$_2$), 1650–1610 and 1568 cm$^{-1}$ (purine ring and olefin), 1010 cm$^{-1}$ (cyclopropane ring).
$^1$H NMR (CD$_3$SOCD$_3$) δ 1.37 (ddd, 1) and 1.71 (td, 1, H$_{4'}$), 1.96 (dqd, 1, H$_{3'}$), 3.40 (d of AB system, 2, H$_{5'}$), 4.82 (t, 1, OH), 7.01 (s, 2, NH$_2$), 7.31 (q, 1, H$_{1'}$), 8.48 (s, 1, H$_8$ of purine).
$^{13}$C NMR (CD$_3$SOCD$_3$) ppm 9.79 (H$_{4'}$), 18.16 (C$_{3'}$), 63.52 (C$_{5'}$), 110.44 (C$_{1'}$), 117.37 (C$_{2'}$); purine ring: 123.51 (C$_5$), 140.00 (C$_8$), 150.05 (C$_4$), 152.99 (C$_2$), 160.48 (C$_8$).
EI-MS 251 and 253 (M, 36.1, 12.3), 234 and 236 (84.0, 29.7), 222 and 224 (8.6, 3.4), 198 (24.6), 170 and 172 (100.0, 37.8).
Calculated for $C_{10}H_{10}ClN_5O$: C, 47.80; H, 4.01; Cl, 13.93; N, 27.89. Found: C, 47.88; H, 4.10; Cl, 14.02; N, 27.91.

EXAMPLE 8

Synthesis of Synguanol (1, B=guanin-$N^9$-yl) and anti-$N^9$-(2-Hydroxymethylcyclopropylidenemethyl) guanine (2, B=guanin-$N^9$-yl).

The solution of the syn isomer 1 (B=2-amino-6-chloropurin-$N^9$-yl, 179 mg, 0.78 mmol) from Example 7 in aqueous formic acid (80%, 10 mL) was heated at 80° C. (bath temperature) with stirring for 3.5 hours. After cooling, the volatile components were evaporated, the residue was dissolved in water (20 mL) and the solution was lyophilized. The resultant white solid was suspended in methanol—concentrated aqueous ammonia (3:1, 40 mL) and the mixture was stirred overnight at room temperature. The solvents were evaporated, and suspension of the residue in methanol (70 mL) was refluxed for 2 hours. The mixture was kept overnight at 0° C. to give synguanol (1, B=guanin-$N^9$-yl, 155 mg, 85% yield).

Mp.>300° C.
UV (ethanol) max 271 nm ($\epsilon$ 11,600), 229 nm ($\epsilon$ 29,400).
IR (KBr) 3450 (flat peak), 3320 and 3170 cm$^{-1}$ (OH and NH$_2$), 1725, 1690, 1640 and 1600 cm$^{-1}$ (guanine ring and olefin), 1020 cm$^{-1}$ (cyclopropane ring).
$^1$H NMR (CD$_3$SOCD$_3$) δ 1.17 (ddd, 1) and 1.45 (td, 1, H$_{4'}$), 2.07 (dqd, 1, H$_{3'}$ of cyclopropane), 3.32 (t, overlapped with H$_2$O at 3.30, 1) and 3.68 (dd, 1, H$_{5'}$), 5.04 (broad s, 1, OH), 6.51 (s, 2, NH$_2$), 7.11 (d, 1, H$_{1'}$), 8.31 (s, 1, H$_8$ of purine), 10.65 (s, 1, NH).
$^{13}$C NMR (CD$_3$SOCD$_3$) ppm 6.60 (C$_{4'}$), 19.56 (C$_{3'}$), 63.23 (C$_{5'}$), 110.59 (C$_{1'}$), 115.44 (C$_{2'}$); guanine ring: 116.68 (C$_5$), 134.70 (C$_8$), 150.12 (C$_4$), 154.33 (C$_2$), 157.11 (C$_6$).
FAB-MS (thioglycerol matrix) 342 (M+thioglycerol+H, 10.4), 234 (M+H, 3.9), 233 (M, 0.9), 232 (M–H, 3.9), 216 (6.6), 197 (15.3), 181 (52.0).
Calculated for $C_{10}H_{11}N_5O_2$: C, 51.48; H, 4.76; N, 30.04. Found: C, 51.60; H, 4.90; N, 29.89.

The procedure described above was used for the synthesis of the anti isomer 2 (B=guanin-$N^9$-yl, 120 mg, 83% yield) starting from the chloropurine intermediate 10 (B=2-amino-6-chloropurin-$N^9$-yl, 150 mg, 0.60 mmol) from Example 7.

Mp.>300° C.
UV (ethanol) max 270 nm ($\epsilon$ 11,900), 228 nm ($\epsilon$ 30,300).
IR (KBr) 3440–3300 and 3150 cm$^{-1}$ (OH and NH$_2$), 1710–1640, and 1610 cm$^{-1}$ (guanine ring and olefin), 1030 cm$^{-1}$ (cyclopropane ring).
$^1$H NMR (CD$_3$SOCD$_3$) a 1.31 (ddd, 1) and 1.66 (td, 1, H$_{4'}$), 1.92 (dqd, 1, H$_{3'}$), 3.37 (dd, 2, H$_{5'}$), 4.80 (broad s, 1, OH), 6.52 (s, 2, NH$_2$), 7.21 (q, 1, H$_{1'}$), 8.04 (s, 1, H$_8$ of purine) and 10.66 (s, 1, NH).
$^{13}$C NMR (CD$_3$SOCD$_3$) ppm 9.55 (C$_{4'}$), 17.91 (C$_{3'}$), 63.58 (C$_{5'}$), 110.75 (C$_{1'}$), 115.89 (C$_{2'}$); guanine ring: 116.68 (C$_5$), 134.16 (C$_8$), 150.29 (C$_4$), 154.35 (C$_2$) and 157.10 (C$_6$)
FAB-MS (thioglycerol matrix) 342 (M+thioglycerol+H, 44.5), 234 (M+H, 35.5), 216 (9.6), 197 (10.3), 181 (41.8), 152 (46.0), 91 (64.8), 73 (100.0).

Calculated for $C_{10}H_{11}N_5O_2 \cdot 0.5H_2O$: C, 49.58; H, 4.99; N, 28.91. Found: C, 49.34; H, 5.09; N, 28.70.

EXAMPLE 9

Synthesis of syn-2,6-Diamino-$N^9$-(2-hydroxymethylcyclopropylidenemethyl)purine (1, B=2,6-diaminopurin-$N^9$-yl).

A mixture of compound 1 (B=2-amino-6-chloropurin-$N^9$-yl, 140 mg, 0.56 mmol) from Example 7 and ammonia in methanol (saturated at 0° C., 80 mL) was heated in a stainless steel bomb at 95° C. (bath temperature) for 16 hours. After cooling, the volatile components were evaporated and the residue was chromatographed on silica gel with dichloromethane—methanol (4:1) to give the title compound 1 (B=2,6-diaminopurin-$N^9$-yl, 105 mg, 81.4% yield) as a white solid.

Mp. 218–221° C.

UV (ethanol) max 280 nm ($\epsilon$ 9,300), 220 nm ($\epsilon$ 27,900).

IR (KBr) 3495,3430,3360 and 3160 cm$^{-1}$ ($NH_2$ and OH), 1660,1630 and 1600 cm$^{-1}$ (purine ring), 1035 and 793 cm$^{-1}$ (cyclopropane ring).

$^1$H NMR ($CD_3SOCD_3$) a 1.16 (ddd, 1) and 1.44 (td, 1, $H_{4'}$), 2.10 (dqd, 1, $H_{3'}$), 3.33 (dt, overlapped with $H_2O$ at 3.30,1) and 3.67 (dt, 1, $H_{1'}$), 5.07 (t, 1, OH), 5.87 (s, 2, 2—$NH_2$), 6.76 (s, 2,6-$NH_2$), 7.16 (d, 1, $H_{1'}$), 8.31 (s, 1, $H_8$ of purine).

$^{13}$C NMR ($CD_3SOCD_3$) ppm 6.65 ($C_{4'}$), 19.62 ($C_{3'}$), 63.43 ($C_{5'}$), 110.83 ($C_{1'}$), 113.22 ($C_{2'}$); purine ring: 113.86 ($C_5$), 134.67 ($C_8$), 150.82 ($C_4$), 156.58 ($C_2$), 161.01 ($C_6$).

EI-MS 232 (M, 45.2), 215 (39.7), 202 (18.5), 198 (10.8), 173 (7.9), 163 (10.9), 159 (9.5), 150 (100.0).

HRMS Calculated for $C_{10}H_{12}N_6O$: M 232.1072. Found: M 232.1076.

Calculated for $C_{10}H_{12}N_6O$: C, 51.70; H, 5.21; N, 36.20. Found: C, 51.53; H, 5.35; N, 36.35.

EXAMPLE 10

Synthesis of syn-2-Amino-6-cyclopropylamino-$N^9$-(2-hydroxymethylcyclopropylidenemethyl)purine (1, B=2-amino-6-cyclopropylaminopurin-$N^9$-yl).

A solution of compound 1 (B=2-amino-6-chloropurin-$N^9$-yl, 151 mg, 0.60 mmol) and cyclopropylamine (0.416 mL, 6.0 mmol) in ethanol (15 mL) was refluxed for 24 hours. After cooling, the volatile components were evaporated and the residue was chromatographed on silica gel with dicholormethane-methanol (95:5→9:1) to give the title compound 1 (B=2-amino-6-cyclopropylaminopurin-$N^9$-yl, 156 mg, 95.5% yield) as a white solid.

Mp. 190–193° C.

UV (ethanol) max 285 nm ($\epsilon$ 16,000), 224 nm ($\epsilon$ 40,000).

IR (KBr) 3475, 3330 and 3200 cm$^{-1}$ ($NH_2$ and OH) and 1640–1595 cm$^{-1}$ (olefin and purine ring), 1043 cm$^{-1}$ (cyclopropane ring).

$^1$H NMR ($CD_3SOCD_3$) δ 0.52–0.59 (m, 2) and 0.63 (d t, 2, $CH_2$ of cyclopropylamino group), 1.14 (ddd, 1) and 1.43 (t d, 1, $H_{4'}$), 2.06 (dqd, 1, $H_{3'}$), 3.00 (broad s, 1, CH of cyclopropylamino group), 3.32 (m, overlapped with $H_2O$ at 3.32, 1) and 3.66 (qt, 1, $H_{5'}$), 5.05 (t, 1, OH), 5.94 (s, 2, 2—$NH_2$), 7.16 (d, 1, $H_{1'}$), 7.38 (d, 1, 6-NH), 8.30 (s, 1, $H_8$).

$^{13}$C NMR ($CD_3SOCD_3$) ppm 6.60 ($C_{4'}$), 6.84 ($CH_2$ of the cyclopropylamino group), 19.57 ($C_{3'}$), 63.41 ($C_{5'}$), 110.79 ($C_{1'}$), 113.44 ($C_{2'}$), 113.88 ($C_5$), 134.44 ($C_8$), 150.31 ($C_4$), 156.33 ($C_2$) and 160.91 ($C_6$).

EI-MS 272 (M, 93.8), 257 (34.9), 255 (29.5), 242 (13.2), 227 (23.8), 213 (15.5), 189 (33.1), 175 (59.5), 162 (25.1), 134 (30.1), 43 (100.0).

HRMS Calculated for $C_{13}H_{16}N_6O$: M 272.1386. Found: 272.1384.

Calculated for $C_{13}H_{16}N_6O$: C, 57.32; H, 5.93; N, 30.87. Found: C, 57.10; H, 6.07; N, 30.63.

EXAMPLE 11

Synthesis of syn-$N_1$-(2-Carbomethoxycyclopropylidenemethyl)cytosine (11, B=cytosin-$N^1$-yl, R=methyl) and anti-$N^1$-(2-Carbomethoxy-cyclopropylidenemethyl)cytosine (12, B=cytosin-$N^1$-yl, R=methyl).

A mixture of $N^4$-acetylcytosine (8, B=$N^4$-acetylcytosin-$N^1$-yl, 3.37 g, 22 mmol), dibromoesters 6 and 7 from Example 1 (6.92 g, 24.2 mmol) and potassium carbonate (15.20 g, 110 mmol) was heated to 100° C. (bath temperature) with stirring under nitrogen for 3 hours. The mixture was cooled to 50° C. and methanol (10 mL) was added with stirring which was continued at 50° C. for another hour. The insoluble portion was filtered off using a Celite bed and it was washed with dichloromethane-methanol (4:1, 3×30 mL). The filtrate was evaporated and the residue was chromatographed on a silica gel column (85 g) using dichloromethane-methanol (9:1) as an eluent to give a mixture of methyl esters 11 and 12 (B=cytosin-$N^1$-yl, R=$CH_3$, 2.28 g, 46.8% yield) as a pale yellow solid. Their ratio was 7:3 as determined by $^1$H NMR. Crystallization from ethyl acetate-ethanol (5:2) or ethanol afforded pure syn isomer (1.31 g, 26.9% yield).

Mp. 221–223° C.

UV (ethanol) max 295 nm ($\epsilon$ 12,500), 230 nm ($\epsilon$ 12,000), 205 nm ($\epsilon$ 14,700).

IR (KBr) 3360 and 3110 cm$^{-1}$ ($NH_2$), 1750 cm$^{-1}$ (C=O, ester), 1670, 1635 and 1490 cm$^{-1}$ (cytosine ring and olefin).

Calculated for $C_{10}H_{11}N_3O_3$: C, 54.28; H, 5.01; N, 19.00. Found: C, 54.56; H, 5.25; N, 18.79.

The mother liquor was evaporated and the residue was recrystallized from ethanol to give a mixture of esters 11 and 12 (B=cytosin-$N^1$-yl, R=methyl, 550 mg, 11.3% yield) in the ratio of 1:2.

Mp. 192–207° C.

UV (ethanol) max 295 nm ($\epsilon$12,100), 230 nm ($\epsilon$11,500), 205 nm ($\epsilon$ 14,700).

IR (KBr): 3340 and 3100 cm$^{-1}$ ($NH_2$), 1750 cm$^{-1}$ (C=O, ester), 1670, 1635 and 1485 cm$^{-1}$ (cytosine ring and olefin).

$^1$H NMR ($CD_3SOCD_3$) a, syn isomer 11 (B=cytosin-$N^1$-yl, R=methyl) 1.76 (ddd, 1) and 1.79 (td, 1, $H_{4'}$), 2.76 (ddd, 1, $H_{3'}$), 3.59 (s, 3, $OCH_3$), 5.81 (d, 1, $H_5$), 7.35 (s, 1, $H_{1'}$), 7.44 (s, 2, $NH_2$), 7.65 (d, 1, $H_6$); anti isomer 12 (B=cytosin-$N^1$-yl, R=methyl) 1.92 (ddd, 1) and 2.03 (td, 1, $H_{4'}$), 2.44 (ddd, 1, $H_{3'}$), 3.59 (s, 3, $OCH_3$), 5.84 (d, 1, $H_5$), 7.44 (s, 3, $NH_2$ and $H_{1'}$), 7.95 (d, 1, $H_6$).

$^{13}$C NMR ($CD_3SOCD_3$) ppm, syn isomer 11 (B=cytosin-$N^1$-yl, R=methyl) 9.26 ($C_{4'}$), 18.30 ($C_{3'}$), 52.33 ($OCH_3$), 108.96 ($C_{2'}$)116.50 ($C_{1'}$), 171.32 (C=O); cytosine ring: 96.01($C_5$), 140.30 ($C_6$), 154.19 ($C_4$), 165.912 ($C_2$); anti isomer 12 (B=cytosin-$N^1$-yl, R=methyl) 12.54 ($C_{4'}$), 15.50 ($C_{3'}$), 52.57 ($OCH_3$), 108.91 ($C_{2'}$), 117.01 ($C_{1'}$); cytosine ring: 172.06 (C=O), 96.11 ($C_5$), 140.48 ($C_6$), 154.24 ($C_4$), 165.92 ($C_2$).

EI-MS 221 (M, 16.5), 206 (9.8), 190 (9.8), 162 (100.0), 135 (8.9), 119 (23.1), 111 (15.4).

EXAMPLE 12

Synthesis of syn-$N^1$-(2-Hydroxymethylcyclopropylidenemethyl)cytosine (1, B=cytosin-$N^1$-yl) and anti-$N^1$-(2-Hydroxymethyl-cyclopropylidenemethyl)cytosine (2, B=cytosin-$N^1$-yl).

A solution of diisobutylaluminum hydride in cyclohexane (1 M, 35.2 mL, 35.2 mmol) was added dropwise into stirred suspension of 1:2 mixture of esters 11 and 12 (B=cytosin-$N^1$-yl, R=methyl, 1.73 g, 7.82 mmol) from Example 11 in tetrahydrofuran (230 mL) within 15 min at 0° C. under nitrogen. After 4 hours, another portion of diisobutylaluminum hydride (11.7 mL, 11.7 mmol) was added. The stirring was continued at 0° C. for another 2 hours. The reaction was quenched by adding methanol-water (2:1, 30 mL) dropwise at 0° C. The mixture was then stirred overnight at room temperature. The gel-like solid was filtered off and it was washed with dichloromethane-methanol (1:1, 5×60 mL) with the aid of a sonicator. The combined filtrate and washings were evaporated to give a mixture of crude products 1 and 2 (B=cytosin-$N^1$-yl, 1.56 g) as a pale yellow solid.

This mixture (7.82 mmol) was dissolved in refluxing ethanol (200 mL). Benzoic anhydride (1.77 g, 7.82 mmol) was added with stirring into a hot solution and the refluxing was continued for 1 h. Five more portions of benzoic anhydride (1.77 g, 7.82 mmol each) were added every hour. After cooling, the solvent was evaporated to give a pale yellow solid which was partitioned between dichloromethane (150 mL) and saturated aqueous sodium hydrogen carbonate (150 mL). The aqueous phase was extracted with dichloromethane (3×50 mL). The combined organic phases were washed with a mixture of saturated aqueous sodium hydrogen carbonate—saturated aqueous sodium chloride (1:3, 40 mL) and they were dried over sodium sulfate. Removal of the solvents left a pale yellow solid which was chromatographed on a silica gel column using dichloromethane—methanol (98:2 and 95:5) to give O,N-dibenzoylated compounds (synlanti mixture, 625 mg, 20% yield), $N^4$-benzoylated syn isomer (1, B=$N^4$-benzoylcytosin-$N^1$-yl, 480 mg, 20.7% yield), and $N^4$-benzoylated anti isomer (2, B $N^4$-benzoylcytosin-$N^1$-yl, 960 mg, 41.4% yield). Both isomers were recrystallized from ethanol.

Syn isomer 1 (B=$N^4$-benzoylcytosin-$N^1$-yl):

Mp. 189–193° C.

UV (ethanol) max 331 ($\epsilon$ 14,800), 270 nm ($\epsilon$ 19,200), 220 nm ($\epsilon$ 15,400), 206 nm ($\epsilon$ 17,200).

IR (KBr) 3370 cm$^{-1}$ (OH), 1695, 1665–1620, 1560 and 1490 cm$^{-1}$ ($N^4$-benzoylcytosine and olefin), 1050 cm$^{-1}$ (cyclopropane ring).

$^1$H NMR (CD$_3$SOCD$_3$) $\delta$ 1.15 (ddd, 1) and 1.41 (td, 1, H$_{4'}$), 2.14 (dqd, 1, H$_{3'}$), 3.31 (dt, overlapped with H$_2$O at 3.33, 1) and 3.65 (dt, 1, H$_{5'}$), 5.01 (dd, 1, OH), 7.37 (s, overlapped with H$_5$, 1, H$_{1'}$), 7.38 (d, overlapped with H$_{1'}$, 1, H$_5$), 8.62 (d, 1, H$_6$), 11.30 (s, 1, NH), 7.50 (t, 2, meta-H), 7.61 (t, 1, para-H), and 7.99 (d, 2, ortho-H of C$_6$H$_5$).

$^{13}$C NMR (CD$_3$SOCD$_3$) ppm 5.91 (C$_{4'}$), 19.44 (C$_{3'}$), 63.05 (C$_{5'}$), 115.76 (C$_{1'}$), 117.51 (C$_{2'}$); benzoyl group: 128.90 (ortho- and meta-C), 133.23 (para-C) and 133.50 (ipso-C of C$_6$H$_5$), 167.78 (C=O); cytosine ring: 97.12 (C$_5$), 145.33 (C$_6$), 153.97 (C$_4$), 163.51 (C$_2$).

EI-MS 297 (M, 10.4), 280 (15.9), 266 (10.1), 216 (6.7), 176 (6.9), 162 (4.8), 122 (7.3), 105 (100.0).

HRMS Calculated for C$_{16}$H$_{15}$N$_3$O$_3$: M 297.1113. Found: M 297.1108.

Calculated for C$_{16}$H$_{15}$N$_3$O$_3$: C, 64.62; H, 5.09; N, 14.14. Found: C, 64.50; H, 5.26; N, 14.18.

Anti isomer 2 (B=$N^4$-benzoylcytosin-$N^1$-yl):

Mp. 177–181° C.

UV (ethanol) max 330 nm ($\epsilon$ 14,600), 269 nm ($\epsilon$ 19,600), 218 nm ($\epsilon$ 14,800), 206 nm ($\epsilon$ 17,200).

IR (KBr) 3300 cm$^{-1}$ (OH), 1695, 1650, 1620, 1570 and 1485 cm$^{-1}$ ($N^4$-benzoyl-cytosine and olefin), 1040 cm$^{-1}$ (cyclopropane ring).

$^1$H NMR (CD$_3$SOCD$_3$) $\delta$ 1.36 (ddd, 1) and 1.67 (td, 1, H$_{4'}$), 1.86 (dqd, 1, H$_{3'}$), 3.38 (dt, 2, H$_{5'}$), 4.82 (t, 1, OH), 7.44 (d, 1, H$_{1'}$), 7.41 (d, 1, H$_5$), 8.46 (d, 1, H$_6$), 11.30 (s, 1, NH), 7.50 (t, 2, meta-H), 7.61 (t, 1, para-H), and 7.99 (d, 2, ortho-H of C$_6$H$_5$).

$^{13}$C NMR (CD$_3$SOCD$_3$) ppm 9.03 (C$_{4'}$), 16.68 (C$_{3'}$), 63.43 (C$_{5'}$), 115.60 (C$_{1'}$), 117.73 (C$_{2'}$), 128.89 (ortho-C), 128.93 (meta-C), 133.23 (para-C) and 133.49 (ipso-C of C$_6$H$_5$), 167.75 (C=O, benzoyl); cytosine ring: 97.35 (C$_5$), 145.15 (C$_6$), 154.09 (C$_4$), 163.51 (C$_2$).

EI-MS 297 (M, 8.6), 280 (18.7), 266 (12.9), 216 (8.4), 176 (3.3), 162 (2.3), 122 (4.9), 105 (100.0);

HRMS Calculated for C$_{16}$H$_{15}$N$_3$O$_3$: M 297.1113. Found: M 297.1108.

Calculated for C$_{16}$H$_{15}$N303: C, 64.62; H, 5.09; N, 14.14. Found: 64.76; H, 5.04; N, 14.34.

The syn isomer 1 (B=$N^4$-benzoylcytosin-$N^1$-yl, 250 mg, 0.84 mmol) was stirred in methanolic ammonia (20%, 30 mL) at room temperature overnight. Evaporation of the resultant solution left a white solid which was recrystallized from ethanol to give syn isomer 1 (B=cytosin-$N^1$-yl, 125 mg, 77% yield).

Mp. 222–224° C.

UV (ethanol) max 298 nm ($\epsilon$ 13,600), 229 nm ($\epsilon$ 13,500), 204 nm ($\epsilon$ 14,100).

IR (KBr) 3320, 3240, and 3100 cm$^{-1}$ (OH and NH$_2$), 1695, 1620 and 1515 cm$^{-1}$ (cytosine ring and olefin), 1040 cm$^{-1}$ (cyclopropane ring).

$^1$H NMR (CD$_3$SOCD$_3$) a 1.01 (ddd, 1) and 1.30 (td, 1, H$_{4'}$), 2.00 (dqd, 1, H$_{3'}$), 2.80 (dt, overlapped with H$_2$O at 3.32, 1) and 3.53 (dtd, 1, H$_{5'}$), 4.93 (dd, 1, OH), 5.75 (d, 1, H$_5$), 7.25 (s, 1) and 7.30 (overlapped with H$_{1'}$, 1, NH$_2$), 7.30 (q, 1, H$_{1'}$), 8.13 (d, 1, H$_6$).

$^{13}$C NMR (CD$_3$SOCD$_3$) ppm 5.57 (C$_{4'}$), 19.28 (C$_{3'}$), 63.38 (C$_{5'}$), 111.63 (C$_{2'}$), 116.06 (C$_{1'}$); cytosine ring: 95.24 (C$_5$), 140.95 (C$_6$), 154.38 (C$_4$), 165.89 (C$_2$).

EI-MS 193 (M, 10.5), 176 (100.0), 162 (78.5), 149 (4.9), 122 (10.2), 112 (60.9)

HRMS Calculated for C$_9$H$_{11}$N$_3$O$_2$: M 193.0851. Found: M 193.0854.

Calculated for C$_9$H$_{11}$N$_3$O$_2$: C, 55.93; H, 5.74; N, 21.76%. Found: C, 55.78; H, 5.94; N, 21.93%.

The anti isomer 2 (B=$N^4$-benzoylcytosin-$N^1$-yl, 250 mg, 0.84 mmol) was debenzoylated using the procedure described above to give anti isomer 2 (B=cytosin-$N^1$-yl, 132 mg, 81% yield).

Mp. 218–220° C.

UV (ethanol) max 296 nm ($\epsilon$ 12,900), 230 nm ($\epsilon$ 12,900), 205 nm ($\epsilon$ 14,900).

IR (KBr) 3370, 3310 and 3100 cm$^{-1}$ (OH and NH$_2$), 1670,1630 and 1505 cm$^{-1}$ (cytosine ring and olefin), 1025 cm$^{-1}$ (cyclopropane ring).

$^1$H NMR (CD$_3$SOCD$_3$) $\delta$ 1.22 (ddd, 1) and 1.56 (td, 1, H$_{4'}$), 1.74 (dqd, 1, H$_{3'}$), 3.32 (dt, overlapped with H$_2$O at 3.32, 1, H$_{5'}$, 4.75 (dd, 1, OH), 5.79 (d, 1, H$_5$), 7.26 and 7.32 (2s, 2, NH$_2$), 7.37 (q, 1, H$_{1'}$), 7.96 (d, 1, H$_6$).

$^{13}$C NMR (CD$_3$SOCD$_3$) a 8.97 (C$_{4'}$), 16.15 (C$_{3'}$), 63.80 (C$_{5'}$), 111.88 (C$_{2'}$), 115.87 (C$_{1'}$); cytosine ring: 95.38 (C$_5$), 140.69 (C$_6$), 154.50 (C$_4$), 165.87 (C$_2$).

EI-MS 193 (M, 6.7), 176 (100.0), 162 (66.0), 149 (5.5), 122 (13.3), 112 (89.1).

Calculated for $C_9H_1, N_3O_2$: C, 55.93; H, 5.74; N, 21.76. Found: C, 55.74; H, 5.92; N, 21.54.

EXAMPLE 13

Synthesis of Methyl Phenylphosphoro-L-alaninate of syn-$N^9$-(2-Hydroxymethylcyclopropylidenemethyl)adenine (3, B=adenin-$N^9$-yl).

Phenylmethoxyalaninyl phosphorochloridate (13) in tetrahydrofuran (0.184 M, 25 mL, 4.6 mmol) and N-methylimidazole (0.73 mL, 9.20 mmol) were added to a sonicated suspension of synadenol 1 (B=adenin-$N^9$-yl, 200 mg, 0.92 mmol) in pyridine (30 mL) at room temperature. The mixture was then stirred for 3.5 h. The solvents were evaporated and the residue was dried in vacuo at room temperature overnight. Chromatography on a silica gel column using gradient dichloromethane-methanol (95:5→9:1) gave the crude product (300 mg) which was rechromatographed using dichloromethane-methanol (95:5) to furnish compound 3 (B=adenin-$N^9$-yl, 270 mg, 64% yield) as a white powder.

Mp 135–149° C.

UV (ethanol) max 277 nm (shoulder, $\epsilon$ 9,300), 262 nm ($\epsilon$ 13,530), 227 nm ($\epsilon$ 28,560), 213 nm ($\epsilon$ 28,355).

IR (KBr): 3500 cm$^{-1}$ (shoulder), 3360 and 3280 cm$^{-1}$ (shoulder), 3200 and 3140 cm$^{-1}$ (shoulder, NH and NH$_2$), 1750 cm$^{-1}$ (C=O, ester), 1665, 1605 and 1580 cm$^{-1}$ (adenine and benzene rings, olefin), 1265 and 1245 cm$^{-1}$ (P=O), 1040, 1010 and 940 cm$^{-1}$ (phosphoroamidate and cyclopropane).

$^1$H NMR (CD$_3$SOCD$_3$) δ 1.11–1.20 (m, 3, CH$_3$), 1.34–1.43 (m, 1) and 1.56–1.67 (m, 1, H$_{4'}$), 2.30–2.44 (m, 1, H$_{3'}$), 3.51, 3.52 and 3.55 (3s, 3, OCH$_3$), 3.62–3.88 (m, 1, CH of alanine), 3.90–4.23 (m, 2, H$_{5'}$), 5.91–6.05 (m, 1, NH of alanine), 7.06–7.17 (m, 3) and 7.24–7.40 (m, 2, phenyl), 7.35 (s, 2, NH$_2$), 7.41–7.46 (m, 1, H$_{1'}$), 8.16 and 8.17 (2s, 1, H$_2$), 8.45, 8.46 and 8.48 (3s, 1, H$_{1'}$).

$^{13}$C NMR (CD$_3$SOCD$_3$): ppm 7.59 (C$_{4'}$), 17.23, 17.29 and 17.33 (C$_{3'}$), 68.13 and 68.17 (C$_{5'}$), 111.92 (C$_{1'}$), 113.76 and 113.94 (C$_{2'}$); adenine: 118.87 (C$_5$), 137.97 (C$_8$), 148.63 (C$_4$), 153.51 (C$_2$), 156.60 (C$_6$); alanine: 19.96, 20.05 and 20.12 (CH$_3$), 50.08, 50.12 and 50.21 (CH), 52.25 and 52.29 (OCH$_3$), 173.56 and 173.85 (C=O); phenyl: 120.56, 120.61 and 120.65 (meta-C), 124.89 (ortho-C), 129.96 (para-C), 151.05 (ipso-C).

$^{31}$P NMR (CD$_3$SOCD$_3$) ppm 3.46, 3.64, 3.73 and 3.90.

FAB-MS (thioglycerol matrix) 567 (M+thioglycerol+H, 41.0), 459 (M+H, 11.9), 308 (17.5), 281 (14.2), 234 (21.1), 200 (100.0), 136 (adenine+H, 60.5).

Calculated for $C_{20}H_{23}N_6O_5P0.3H_2O$: C, 51.79; H, 5.13; N, 18.12. Found: C, 51.90; H, 5.20; N, 18.14.

EXAMPLE 14

Synthesis of Methyl Phenylphosphoro-L-alaninate of anti-$N^9$-(2-Hydroxymethylcyclopropylidenemethyl)adenine (4, B=adenin-$N^9$-yl).

The procedure described in Example 13 was used on the same scale starting from anti-$N^9$-(2-hydroxymethylcyclopropylidenemethyl)adenine (2, B=adenin-$N^9$-yl). The reaction mixture was stirred at room temperature for 4 h. After removal of solvents, the residue was dissolved in methanol (1 mL) and it was partitioned between ethyl acetate (250 mL) and water (100 mL). The aqueous phase was extracted once with ethyl acetate (60 mL). The combined organic phases were washed with water (4×80 mL) and brine (80 mL). They were dried over Na$_2$SO$_4$ and evaporated to leave a syrup. Chromatography on a silica gel column using gradient dichloromethane—methanol (95:5→92:8) gave compound 4 (B=adenin-$N^9$-yl) as a white foam (328 mg, 74% yield).

Mp 60–77° C.

UV (ethanol) max 277 nm (shoulder, $\epsilon$ 8,930), 262 nm ($\epsilon$ 12,750), 225 nm ($\epsilon$ 28,040), 214 nm (shoulder, $\epsilon$ 27,210).

IR (KBr) 3330 cm$^{-1}$ (br) and 3180 (br, NH and NH$_2$), 1750 cm$^{-1}$ (C=O, ester), 1645, 1600 and 1580 cm$^{-1}$ (adenine and benzene rings, olefin), 1250 cm$^{-1}$ (P=O), 1025 and 937 cm$^{-1}$ (phosphoroamidate and cyclopropane).

$^1$H NMR (CD$_3$SOCD$_3$) δ 1.20 (apparent t, 3, CH$_3$), 1.52–1.65 (m, 1) and 1.78–1.90 (m, 1, H$_{4'}$), 2.18 (m, 1, H$_{3'}$), 3.54, 3.54, 3.56 and 3.58 (4s, 3, OCH$_3$), 3.77–3.93 (m, 1H, CH of alanine), 3.93-4.10 (m, 2, H$_{5'}$), 6.01 (apparent d t, 1, NH of alanine), 7.09–7.23 (m, 3) and 7.29–7.45(m, 2, OC$_6$H$_5$), 7.38 (s, 2, NH$_2$), 7.50–7.56 (m, 1, H$_{1'}$), 8.18 (s, 1, H$_2$), 8.48 and 8.48 (2s, 1, H$_8$).

13C NMR (CD$_3$SOCD$_3$) ppm 10.25 and 10.31 (C$_{4'}$), 15.32 (C$_{3'}$), 68.50 (C$_{5'}$), 111.85 (C$_{1'}$), 114.36 (C$_{2'}$); alanine: 20.02 and 20.10 (CH$_3$), 50.10 and 50.24 (CH of alanine), 52.25 (OCH$_3$), 174.11 and 174.18 (C=O); adenine: 118.84 (C$_5$), 137.65 (C$_8$), 148.71 (C$_4$), 153.54 (C$_2$), 156.49 (C$_6$); phenyl: 120.62 (meta-C), 124.89 (ortho-C), 123.00 (para-C), 151.18 and 151.26 (ipso-C).

31p NMR (CD$_3$SOCD$_3$) ppm 3.55, 3.91 and 3.97.

EI-MS 459 (M+H, 1.5), 458 (M, 6.7), 307 (1.1), 264 (4.1), 200 (100.0), 135 (adenine, 40.8).

HRMS: Calculated for $C_{20}H_{23}N_6O_5P$: M 458.14675; Found: M 458.1477.

Calculated for $C_{20}H_{23}N6O_5P$ 0.4H$_2$O: C, 51.59; H, 5.15; N, 18.05. Found: C, 51.77; H, 5.26; N, 17.86.

EXAMPLE 15

Synthesis of Methyl Phenylphosphoro-L-alaninate of syn-2,6-diamino-$N^9$-(2-Hydroxycyclopropylidene-methyl)purine (3, B=2,6-diaminopurin-$N^9$-yl).

Phenylmethoxyalaninyl phosphorochloridate (13) in tetrahydrofuran (0.184 M, 16.7 mL, 3 mmol) was added dropwise into a suspension of syn-2,6, diamino-(2-hydroxymethylcyclopropylidenemethyl)purine (1, B=2,6, diaminopurin-$N^9$-yl, 140 mg, 0.6 mmol) in pyridine (20 mL) with stirring at room temperature. After 5 min., N-methylimidazole (0.48 mL, 6 mmol) was added and the stirring was continued for 3 h. An insoluble gum which formed was dissolved by addition of pyridine (20 mL) and the reaction mixture was stirred overnight at room temperature. The solvents were evaporated, the residue was dissolved in 80% acetic acid (35 mL) and the solution was allowed to stand at room temperature for 88 h and then it was evaporated. Chromatography of the crude product on a silica gel column using dichloromethane-methanol (95:5) gave a yellow sirup. This product was dissolved in a mixture of methanol (20 mL) and 0.1 M Na$_2$HPO$_4$ (pH 7.5, 20 mL). The solution was stirred overnight at room temperature, it was then evaporated and the product was rechromatographed as shown above. The obtained hygroscopic gum was dissolved in methanol (1 mL), water (10 mL) was added and the resultant suspension was lyophilized to give compound 3 (B=2,6-diaminopurin-$N^9$-yl, 170 mg, 60%) as a white solid.

Mp 65–83C.

UV (EtOH) max 280 nm ($\epsilon$ 11,800), 229 nm ($\epsilon$ 35,500).

IR (KBr) 3350 and 3200 cm$^{-1}$ (NH and NH$_2$), 1745 cm$^{-1}$ (C=O, ester), 1670–1580 cm$^{-1}$ (olefin, purine and benzene ring), 1220 cm$^{-1}$ (P=O), 1160 cm$^{-1}$ (C=O), 1020 and 940 cm$^{-1}$ (phosphoramidate and cyclopropane).

$^1$H NMR (CD$_3$SOCD$_3$) $\delta$ 1.12–1.22 (m, 3, CH$_3$), 1.27–1.38 (m, 1) and 1.50–1.62 (m, 1, H$_4$), 2.22–2.40 (m, 1, H$_3$), 3.52 and 3.55 (2s, 3, OCH$_3$), 3.68–3.88 (m, 1, Ala-CH), 3.88–4.05 (m, 1) and 4.10–4.30 (m, 1, H$_5$), 5.91 (s, 2,2-NH$_2$), 5.85–6.06 (m, 1, NH), 6.79 (s, 2,6—NH$_2$), 7.08–7.20 (m, 3) and 7.20–7.36 (m, 3, H$_{1'}$ and phenyl), 8.037, 8.040, 8.05, and 8.06 (4s, 1, H$_8$.

$^{13}$C NMR (CD$_3$SOCD$_3$) ppm 7.43, 7.50, and 7.605 (C$_{4'}$), 17.32, 17.41, and 17.80 (C$_{3'}$), 68.25 and 68.405 (C$_{5'}$), 111.77 (C$_{1'}$), 113.26 (C$_{2'}$); alanine: 19.97, 20.06, and 20.12 (CH$_3$), 49.94, 50.07, 50.16, and 50.25 (CH), 52.28 (OCH$_3$), 174.10 and 174.17 (C=O); phenyl: 120.66 (C-meta), 124.93 (C-ortho), 130.00 (C-para), 151.04 and 151.14 (C-ipso); purine: 112.16 (C$_5$), 134.48 and 134.56 (C$_8$), 150.56 and 150.93 (C$_4$), 156.60 (C$_2$), 161.07 (C$_6$).

$^{31}$P NMR (CD$_3$SOCD$_3$) ppm 3.62, 3.85, 3.90 and 4.08.

FAB-MS (thioglycerol matrix) 582 (M+thioglycerol+H, 48.6), 474 (M+H, 11.6), 323 (19.4), 281 (15.7), 249 (27.5), 215 (43.7), 200 (36.2), 151 (2,6-diaminopurine+H, 100.0).

Calculated for C$_{20}$H$_{24}$N$_7$O$_5$P: C, 50.72; H, 5.11; N, 20.72. Found: C, 50.95; H, 5.06; N, 20.49%.

EXAMPLE 16

In vitro Antiviral Evaluation Methods

Cells and viruses. The routine growth and passage of KB cells was performed in monolayer cultures using minimal essential medium (MEM) with either Hanks salts [MEM(H)] or Earle salts [MEM(E)] supplemented with 10% calf serum. The sodium bicarbonate concentration was varied to meet the buffering capacity required. Cultures of diploid human foreskin fibroblasts (HFF) or MRC-5 cells were grown in medium consisting of MEM(E) with 10% fetal bovine serum. Cells were passaged at 1:2 to 1:10 dilutions according to conventional procedures by using 0.05% trypsin plus 0.02% EDTA in a HEPES buffered salt solution (HBS) (Shipman, C., Jr., *Proc. Soc. Exp. Biol.* 130:305–310 (1969)) as described previously. Turk, S. R., et al., *Antimicrob. Agents Chemother.* 31:544–550 (1987). HFF and MRC-5 cells were passaged only at 1:2 dilutions. CEM cells were maintained in suspension culture as detailed previously. Kucera, L. S., et al., *AIDS Res. Human Retroviruses* 9:307–314 (1993).

Virological procedures. Stock HCMV was prepared by infecting HFF cells at a multiplicity of infection (m.o.i.) of <0.01 plaque-forming units (p.f.u.) per cell. Cell growth medium was changed every four days until cytopathology was evident in all cells (approximately 21 days). Supernatant fluids were retained as the virus stock. High titer HSV-1 stocks were prepared by infecting KB cells at an m.o.i. of <0.1 as detailed previously. Turk, S. R., et al., Antimicrob. Agents Chemother. 31:544–550 (1987). Virus titers were determined using monolayer cultures of HFF cells for HCMV and monolayer cultures of BSC-1 cells for HSV-1 as described earlier. Prichard, M. N., et al., *J. Virol. Methods* 28:101–106 (1990). Briefly, HFF or BSC-1 cells were planted as described above in 96-well cluster dishes and incubated overnight at 37° C. in a humidified 3% CO$_2$–97% air atmosphere. The next day cultures were inoculated with HCMV or HSV-1 and serially diluted 1:3 across the remaining eleven columns of the 96-well plate. Cultures were incubated at 37° C. for 2 hr to permit virus adsorption and then virus inoculum was replaced with 0.2 mL of fresh medium. Cultures were incubated for seven days for HCMV, two or three days for HSV-1, medium was removed, and the cell sheets were stained with 0.1% crystal violet in 20% methanol. Plaques were enumerated under 20-fold magnification in wells having the dilution which gave 5 to 20 plaques per well. Virus titers were calculated according to the following Formula: Titer (p.f.u./mL)=number of plaques x 5×3$^n$; where n represents the nth dilution of the virus used to infect the well in which plaques were enumerated.

Assays for Antiviral Activity.

(a) HCMV. The effect of compounds on the replication of HCMV has been measured using a plaque reduction assay. HFF cells in 24-well cluster dishes were infected with approximately 100 p.f.u. of HCMV per cm$^2$ cell sheet using the procedures detailed above. Following virus adsorption, compounds dissolved in growth medium were added to duplicate wells in three to six selected concentrations. Following incubation at 37° C. for 7 to 10 days, cell sheets were fixed, stained with crystal violet and microscopic plaques enumerated as described above. Drug effects were calculated as a percentage of reduction in number of plaques in the presence of each drug concentration compared to the number observed in the absence of drug. Ganciclovir (DHPG) was used as a positive control in all experiments. The effect of compounds on the replication of HCMV also was measured using a yield reduction assay. HFF cells were planted as described above in 96-well cluster dishes, incubated overnight, medium removed and the cultures were inoculated with HCMV at a m.o.i. of 0.5 to 1 p.f.u. per cell as reported elsewhere. After virus adsorption, inoculum was replaced with 0.2 mL of fresh medium containing test compounds. The first row of 12 wells was left undisturbed and served as virus controls. Each well in the second row received an additional 0.1 mL of medium with test compound at three times the desired final concentration. The contents of the 12 wells were mixed by repeated pipetting and then serially diluted 1:3 along the remaining wells. In this manner, six compounds could be tested in duplicate on a single plate with concentrations from 100 $\mu$M to 0.14 $\mu$M. Plates were incubated at 37° C. for seven days, subjected to one cycle of freezing and thawing; aliquots from each of the eight wells of a given column were transferred to the first column of a fresh 96-well monolayer culture of HFF cells. Contents were mixed and serially diluted 1:3 across the remaining eleven columns of the secondary plate. Each column of the original primary plate was diluted across a separate plate in this manner. Cultures were incubated, plaques were enumerated, and titers calculated as described above.

(b) HSV-1. An enzyme-liked immunosorbent assay (ELISA) was employed to detect HSV-1. 96-well cluster dishes were planted with BSC-1 cells at 10,000 cells per well, in a total volume of 200 $\mu$L per well of MEM(E) plus 10% calf serum. After overnight incubation at 37° C., drug and HSV-1 was added at the rate of 100 PFU/well. ELISA plates were blocked with 200 $\mu$L per well of 10% calf serum and 0.05% tween in HBS. After incubation for 30 minutes, the blocking agent was rinsed two times with HBS-T. A 1:400 dilution of AP conjugated rabbit anti-HSV-1 antibody in HBS-F was added. Plates were sealed with adhesive sheet, and incubated on rocker for one hour at 37° C. Plates were developed in the dark with 100 $\mu$L per well of substrate solution containing p-nitrophenyl phosphate. Plates were read at 492 nm. Drug effects were calculated as a percentage of the reduction in virus in the presence of each drug concentration compared to the titer obtained in the absence of drug. Acyclovir was used as a positive control in all experiments.

(c) HHV-6. In this case, enzyme-linked immunosorbent assay (ELISA) was performed in covalent amine plates (Costar, Cambridge, Mass.). The plates were activated by the addition of a homobifunctional crosslinking agent, bis (sulfosuccinimidyl) suberate, which was dissolved at 1 mg/mL in 30 mL of phosphate buffered saline (PBS: 137 mM NaCl, 2.7 mM KCl, 4.3 mM $Na_2HPO_4$, 1.4 mM $KH_2PO_4$, pH 7.4) and 300 µL of the crosslinker was added to each well in the covalent plate. The crosslinker reacted with the amine function on the plate for 30 min at room temperature. The byproduct, sodium N-hydroxysuccinimide sulfite, was removed by decanting and washing the plate twice with PBS. Samples consisting of 150 µl of mixed suspended $HSB_2$ cells from the original drug-treated plate were solubilized in an equal volume of 10% Triton X-100 in coating buffer (15 mM $Na_2CO_3$, 3.5 mM $NaHCO_3$, pH 9.6). The plate was covered and then incubated for 1 h at 37° C. in a 5% $CO_2$ atmosphere. These binding conditions facilitated covalent attachment of the antigen to the free end of the crosslinker.

After covalent binding, the antigen solution was decanted and the plate was washed six times in HEPES buffered saline (Shipman, C., Jr., *Proc. Soc. Exp. Biol.* 130:305–310 (1969)) with 0.05% Tween 20 (HBS-T), soaking for three min for each wash. Unbound sites on the plate were blocked with 300 µL per well of 2% lowfat dry milk in PBS (blocker) for 30 min at room temperature on a shaker. The blocker was decanted and 50 µL of the diluted primary monoclonal antibody, specific for HHV-6 (GS) glycoprotein gp116, was added. The antibody solution consisted of antibody diluted 1:400 in equal volumes of blocker and 10% Triton X-100 in coating buffer. The presence of both blocker and detergent in the antibody solutions was necessary to reduce background signal. The plate was then covered and incubated for 1 h at 37° C. The plate was washed again, as described above, then blocker was added again, as before. Next, each well received 100 µL of a solution of the secondary antibody, horse radish peroxidase-labeled rabbit anti-mouse antibody, diluted to 1:400 (as above). The plate was incubated for 1 h at 37° C. The plate was washed again as described above, and developed using 100 µL/well of TMB-Turbo (Pierce, Rockford, Ill.) for 30 min at room temperature. The reaction was stopped with 50 µL/well 2 M $H_2SO_4$. Absorbance in each well was determined at 450/570 nm.

(d) HIV-1. Reverse transcriptase (RT) was employed as a marker for HIV-1. This assay measured the presence of HIV in supernatants of CEM cells infected with strain $III_B$ of HIV-1 by the amount of RT activity. Cells were grown, infected, and incubated in the presence of seven concentrations (one-half $log_{10}$ dilutions) beginning at 1 or 100 µM of compounds to be assayed. Procedures and the RT assay were performed as detailed previously. Kucera, L. S., et al., *AIDS Res. Human Retroviruses* 9:307–314 (1993); White, E. L., et al., *Antiviral Res.* 16:257–266 (1991).

Cytotoxicity assays. Two different assays were used to explore cytotoxicity of selected compounds as we have detailed previously. (Q) Cytotoxicity produced in stationary HFF cells and in growing CEM cells was determined by microscopic inspection of cells used in plaque and RT assays which were not affected by the virus. Turk, S. R., et al., *Antimicrob. Agents Chemother.* 31:544–550 (1987). (ii) The effect of compounds during two population doublings of KB cells was determined by crystal violet staining and spectrophotometric quantitation of dye eluted from stained cells. Prichard, M. N., et al., *Antimicrob. Agents Chemother.* 35:1060–1065 (1991).

Data Analysis. Dose-response relationships were constructed by linearly regressing the percent inhibition of parameters derived in the preceding sections against log drug concentrations. Fifty-percent inhibitory ($IC_{50}$) concentrations were calculated from the regression lines. Samples containing positive controls (acyclovir for HSV-1, ganciclovir for HCMV, and 2-acetylpyridine thiosemicarbazone for cytotoxicity) were used in all assays.

Testing Results. Compounds of Formula 1 exhibit a significant activity against herpes viruses. It was found that compounds of the present invention strongly inhibit the replication of HMCV as measured by plaque and yield reduction assays using HFF as host cells by the method described above and they also inhibit the replication of HSV-1 as determined by enzyme-linked immunosorbent assay (ELISA).

| Compound | HCMV[a] | $IC_{50}(\mu M)$ HCMV[b] | HSV-1[c] |
|---|---|---|---|
| 1 (B = adenine), Example 5 | 2.0 | 1.5 | 3.7 |
| 1 (B = guanine), Example 8 | 2.0 | 1.8 | 100 |
| 1 (B = cytosine), Example 12 | 28 | 16 | >100 |
| 1 (B = 2,6-diaminopurine), Example 9 | 15 | 18 | >100 |
| 1 (B = 2-amino-6-cyclopropylaminopurine), Example 10 | 0.4 | 1.0 | 20 |
| 1 (B = 2-amino-6-chloropurine), Example 7 | 5.0 | 0.8 | 40 |
| 3 (B = adenine), Example 13 | 0.14 | 0.21 | 2.5 |
| 4 (B = adenine), Example 14 | 21 | — | 65 |
| 3 (B = diaminopurine), Example 15 | 4 | — | 50 |

[a]Plaque reduction.
[b]Yield reduction, $IC_{90}$.
[c]ELISA.

These effects are comparable with those of ganciclovir, current drug of choice for HCMV.

Compounds of the present invention also strongly inhibit HHV 6 to a greater extent than current drug foscarnet (Foscavir) as determined by enzyme-linked immunosorbent assay (ELISA) in HSB-2 cells by the method described above.

| Compound | HHV-6, $IC_{50}$ ($\mu M$) |
|---|---|
| 1 (B = adenine), Example 5 | 3.0 |
| Foscarnet | 15.0 |

Compounds of the present invention also inhibit HIV-1 when tested in a reverse transcriptase assay as described above.

| Compound | HIV-1, $IC_{50}$ ($\mu M$) |
|---|---|
| 1 (B = guanine), Example 8 | 1.3 |
| 3 (B = adenine), Example 13 | <0.14 |

-continued

| Compound | HIV-1, IC$_{50}$ ($\mu$M) |
|---|---|
| 4 (B = adenine), Example 14 | 1.6 |
| 3 (B = 2,6-diaminopurine), Example 15 | 0.26 |

In the cell line used to propagate HIV-1, no visual toxicity was observed at 100 $\mu$M.

Compounds of the present invention were tested for cytotoxicity in a culture of HFF and KB cells according to the methods described above.

| | IC$_{50}$ ($\mu$M) | | |
|---|---|---|---|
| Compounds | HFF (visual) | KB (growth) | GEM (visual) |
| 1 (B = adenine), Example 5 | >100 | 82 | >100 |
| 1 (B = guanine), Example 8 | >100 | >100 | >100 |
| 1 (B = cytosine), Example 12 | >100 | >100 | >100 |
| 1 (B = 2,6-diaminopurine), Example 9 | >100 | >100 | >100 |
| 1 (B = 2-amino-6-cyclopropylaminopurine), Example 10 | >100 | >100 | >100 |
| 1 (B = 2-amino-6-chloropurine), Example 7 | >100 | >100 | — |
| 3 (B = adenine), Example 13 | 2.5 | 0.5 | 1.1 |
| 4 (B = adenine), Example 14 | 100 | 50 | 66 |
| 3 (B = 2,6-diaminopurine), Example 15 | >100 | 40 | 100 |

EXAMPLE 17

In vivo Antiviral Evaluation Method

Compounds 1 (B=adenin-N$^9$-yl and guanin-N$^9$-yl) were evaluated in mice infected with murine cytomegalovirus (MCMV). Mice were infected intraperitonealy with sufficient MCMV to produce 90 to 100% mortality. Compounds were administered once daily for five days at doses of 5.6, 16.7 and 50 mg/kg by intraperitoneal injection in a 0.4% suspension of carboxymethylcellulose. Ganciclovir was administered in sterile water at the same doses as a positive control drug. All compounds were administered to separate groups of 15 mice each at 6, 24, and 48 hours after infection with MCMV. Groups of 10 uninfected mice also received test compounds as toxicity controls at the doses listed above.

Compound 1 (B=adenin-N$^9$-yl) reduced mortality from 100% in placebo treated mice to 33% in mice treated with 50 mg/kg of the drug. Decreasing effecis were noted at lower doses and when drug administration was delayed until 24 or 48 hours after infection. No deaths were observed in uninfected mice that received only drug.

In a second experiment, compound 1 (B=guanin-N$^9$-yl) reduced mortality from 90% in placebo treated mice to about 7 to about 13% in mice treated with 16.7 or 50 mg/kg of this drug. No deaths were observed in uninfected mice that received only drug. In a similar manner, ganciclovir reduced mortality to about 0 to about 20% at these doses and it was somewhat more effective than compound 1 (B=guanin-N$^9$-yl) at 5.6 mg/kg.

EXAMPLE 18

Synthesis of syn-2-Amino-6-methoxy-N$^9$-(2-hydroxymethyl-cyclopropylidenemethyl)purine (1, B=2-amino-6-methoxypurin-N$^9$-yl).

A solution of compound 1 (B=2-amino-6-chloropurin-N$^9$-yl, 50 mg, 0.17 mmol) from Example 7 and K$_2$CO$_3$ (84 mg, 0.61 mmol) in methanol—water (9:1, 5 mL) was stirred at room temperature for 60 h. Volatile components were removed by evaporation. The residue was chromatographed on silica gel using dichloromethane—methanol (95:5 →9:1) to give product 1 (B=2-amino-6-methoxypurin-N$^9$-yl) as a white solid (40 mg, 95%).

Mp. 196–199° C.

UV (ethanol) max 280 nm ($\epsilon$ 11,600), 224 nm ($\epsilon$ 31,000).

IR (KBr) 3400, 3310, 3210, and 3100 cm$^{-1}$ (NH$_2$ and OH), 1645 and 1585 cm$^{-1}$ (olefin and purine ring), 1050 cm$^{-1}$ (cyclopropane).

$^1$H NMR (CD$_3$SOCD$_3$) a 1.16 (ddd, 1) and 1.44 (td, 1, H$_{4'}$), 2.07 (dqd, 1, H$_{3'}$), 3.33 (ddd, overlapped with H$_2$O at 3.30, 1) and 3.69 (dt, 1, H$_{5'}$), 3.41 (s, 3H, OCH$_3$), 5.08 (dd, 1, OH), 6.52 (s, 2, NH$_2$), 7.19 (d, 1, H$_{1'}$), 8.47 (s, 1, H$_8$ of purine).

$^{13}$C NMR (CD$_3$SOCD$_3$) ppm 6.59 (C$_{4'}$), 19.57 (C$_{3'}$), 63.68 (C$_{5'}$), 63.33 (OCH$_3$), 110.54 (C$_{1'}$), 115.09 (C$_{2'}$), 113.87 (C$_5$), 136.94 (C$_8$), 152.94 (C$_4$), 160.55 (C$_2$) and 161.13 (C$_6$).

EI-MS 247 (M, 65.4), 230 (63.3), 217 (30.2), 198 (11.8), 178 (10.9), 166 (100.0).

HRMS: Calculated M for C$_{11}$H$_{13}$N$_5$O$_2$ 247.1069; found: 247.1074.

Calculated for C$_{10}$H$_{12}$N$_6$O: C, 53.42; H, 5.30; N, 28.33. Found: C, 53.28; H, 5.19; N, 28.18.

EXAMPLE 19

Synthesis of syn-2-Amino-6-azido-N$^9$-(2-hydroxymethyl-cyclopropylidene-methyl)purine (1, B=2-amino-6-azidopurin-N$^9$-yl.

A mixture of compound 1 (B=2-amino-6-chloropurin-N$^9$-yl, 151 mg, 0.6 mmol) from Example 7 and sodium azide (117 mg, 1.8 mmol) in N,N-dimethylformamide (10 mL) was heated in an oil bath at 107° C. for 4 h. After evaporation of the solvent in vacuo, water (5 ml) was added to the residue to give product 1 (B=2-amino-6-azidopurin-N$^9$-yl) as a white solid (137 mg, 88.4%).

Mp. 184–187° C. (dec.).

UV (ethanol) max 302 nm ($\epsilon$ 11,450), 281 nm (shoulder, $\epsilon$ 9,830), 229 nm ($\epsilon$ 30,330).

IR (KBr): 3440, 3310 and 3140 cm$^1$ (NH$_2$ and OH), 1640–1680 and 1565 cm$^{-1}$ (olefin and purine ring), 1040 and 1020 cm$^{-1}$ (cyclopropane ring). $^1$H NMR (CD$_3$SOCD$_3$) $\partial$ 1.24 (ddd, 1) and 1.51 (td, 1, H$_{4'}$), 2.15 (m, 1H, H$_{3'}$), 3.28–3.38 (m, partially overlapped with H$_2$O at 3.34, 1) and 3.72 (dt, 1, H$_{5'}$), 5.08 (t, 1, OH), 7.32 (d, 1, H$_{1'}$), 8.47 (s, 2H, 2—NH$_2$), 8.74 (s, 1, H$_8$).

$^{13}$C NMR (CD$_3$SOCD$_3$) ppm 6.76 (C$_{4'}$), 19.72 (C$_{3'}$), 63.13 (C$_{5'}$), 110.61 (C$_{1'}$). 111.99 (C$_{2'}$), 117.45 (C$_5$), 137.41 (C$_8$), 143.63 (C$_4$), 144.42 (C$_2$), and 146.48 (C$_6$).

Calculated for C$_{10}$H$_{10}$N$_8$OH$_2$O: C, 43.48; H, 4.38; N, 40.56. Found: C, 43.45; H, 4.23; N, 40.48.

EXAMPLE 20

Synthesis of Ethyl-(R)-Methylenecyclopropanecarboxylate (R)- and (S)-Methylenecyclopropanecarboxylic acids were prepared as described. Lai, M.-T., Liu, L.-D., Liu, H.-W. J. Am. Chem. Soc. 113:7388–7397 (1991).

The (R)-methylenecyclopropanecarboxylic acid (3.92 g, 39.95 mmol) was stirred in ethanolic HCl (1.0 M, 60 mL) at room temperature for 24 h. The solution was diluted with water (60 mL) and then extracted with 1-pentane (8×80 mL). The combined extracts were washed with water, saturated NaHCO$_3$, water and brine (80 mL each). After drying (Na$_2$SO$_4$) the solvents were removed by distillation and the crude product was used directly in the next step.

The S-enantiomer was prepared by the same procedure starting from (S)-methylenecyclopropanecarboxylic acid.

EXAMPLE 21

Synthesis of Ethyl-(2R)-2-Bromo-2-bromomethyl-(1S)-cyclopropane-carboxylate and Ethyl-(2S)-2-Bromo-2-bromomethyl-(1 S)-cyclopropanecarboxylate.

Bromine (2.25 mL, 43.67 mmol) was added into a solution of ethyl-(R)-methylenecyclopropanecarboxylate from Example 20 in CCl$_4$ (80 mL) during 15 min at 0° C. with stirring. After 0.5 h the volatile components were evaporated in vacuo and the excess of bromine was removed with Na$_2$S$_2$O$_3$. A yellowish oil (11.02 g, 96.5% crude yield) thus obtained was pure enough for the next step as shown by $^1$H NMR, which was similar to racemic cis and trans isomers 6 and 7 (Example 1). The HPLC (detection at 220 nm) on Chiralpak AD column in hexane-2-propanol (9:1, 1 mL/min) indicated the presence of two diastereoisomers, t$_R$ (min) 4.34 (1 S, 2S) and 5.65 (1S, 2R).

The 1 R, 2S and 1 R, 2R-diastereoisomers were prepared in a similar fashion, t$_R$4.47 (1R,2S) and 6.02 (1R, 2R).

EXAMPLE 22

Synthesis of R-(−)- and S-(+)-enantiomers of compounds 1 (B=2-amino-6-chloropurin-N$^9$-yl, B= guanin-N$^9$-yl or 2,6-diamino-purin-N$^9$-yl or 2-amino-6-cyclopropyl-aminopurin-N$^9$-yl or 2-amino-6-methoxypurin-N$^9$-yl) and compound 2 (B=2-amino-6-chloropurin-N$^9$-yl).

The reduction of diastereoisomeric esters described in Example 21 followed the procedure for the corresponding racemates of cis and trans isomers. Qiu, Y.-L., Zemlicka, J. Synthesis 1447–1452 (1998). Subsequent acetylation and alkylation of 2-amino-6-chioropurine 8 (B=2-amino-6-chloropurin-N$^9$-yl) with the resultant IR or 1S cis and trans 1-acetoxymethyl-2-bromo-2-bromomethylcyclopropanes was also performed as described for the racemic compounds to give, after deacetylation, the title R- or S-enantiomers. All HPLC determinations of purity and enantiomeric excess were carried out under isocratic conditions on a Chiralpak AD column with methanol as the solvent and a flow rate of 1 mL/min.

R-(−)-enantiomer of compound 1 (B=2-amino-6-chloropurin-N$^9$-yl).
  HPLC:tR=27.23 min, purity 100%, 98.9% ee.
  Mp. 185–187° C.
  [α]$_D^{25}$=−76.1°, c 0.36 (DMF).
  UV (ethanol) max 310 nm (ε 7,970), 234 nm (ε 30,300).
  $^1$H NMR and MS were identical to those reported for the racemic compound 1 (B=2-amino-6-chloropurin-N$^9$-yl) in Example 7.
  HRMS: Calculated M for C$_{10}$H$_{10}$$^{35}$ClN$_5$O 251.0574; found 251.0580.
  Calculated for C$_{10}$H$_{10}$ClN$_5$O: C, 47.80; H, 4.01; N, 27.89; Cl, 13.93. Found: C, 47.56; H, 4.10; N, 27.84; Cl, 14.14.

R-(−)-enantiomer of compound 2 (B=2-amino-6-chloropurin-N$^9$-yl).
  HPLC: t$_R$=8.64 min, purity 100%, 100% ee.
  Mp. 220–223° C.
  [α]$_D^{25}$=−37.4°, c 0.32 (DMF).
  UV (ethanol) max 311 nm (ε 7,730), 232 nm (ε 32,050).
  $^1$H NMR and MS were identical to those reported for the racemic compound 2 (B=2-amino-6-chloropurin-N$^9$-yl) in Example 7.
  HRMS: Calculated M for C$_{10}$H$_{10}$$^{35}$ClN$_5$O 251.0574; found 251.0571.
  Calculated for C$_{10}$H$_{10}$ClN$_5$O: C, 47.80; H, 4.01; N, 27.89; Cl, 13.93. Found: C, 47.44, H, 4.16; N, 27.77; Cl, 14.20.

S-(+)-enantiomer of compound 1 (B=2-amino-6-chloropurin-N$^9$-yl).
  HPLC: t$_R$=5.48 min, purity 100%, 94.2% ee.
  Mp. 188–191° C.
  [α]$_D^{25}$=+74.80, c 0.36 (DMF).
  UV (ethanol) max 310 nm (ε 7,820), 233 nm (ε31,600).
  $^1$H NMR and MS were identical to those reported for the racemic compound 1 (B=2-amino-6-chloropurin-N$^9$-yl) in Example 7.
  HRMS: Calculated M for C$_{10}$H$_{10}$$^{35}$ClN$_5$O 251.0574; found 251.0570.
  Calculated for C$_{10}$H$_{10}$ClN$_5$O: C, 47.80; H, 4.01; N, 27.89; Cl, 13.93. Found: 47.66; H, 3.68; N, 28.00; Cl, 13.76.

S-(+)-enantiomer of compound 2 (B=2-amino-6-chloropurin-N$^9$; yl).
  HPLC: t$_R$=9.74 min, purity 97.0%, contaminated with 2.9% of the S-enantiomer of compound 1 (B=2-amino-6-chloropurin-N$^9$-yl), 98.8% ee.
  Mp. 220–223° C.
  [α]$_D^{25}$=+38.00, c 0.38 (DMF).
  UV (ethanol) max 310 nm (ε 7,730), 232 nm (ε 32,070).
  $^1$H NMR and MS were identical to those reported for the racemic compound 2 (B=2-amino-6-chloropurin-N$^9$-yl) in Example 7.
  HRMS: Calculated M for C$_{10}$H$_{10}$$^{35}$ClN$_5$O 251.0574; found 251.0572.
  Calculated for C$_{10}$H$_{10}$ClN$_5$O: C, 47.80; H, 4.01; N, 27.89; Cl, 13.93. Found: 48.10; H, 4.26; N, 28.03; Cl, 13.84.

R- and S-enantiomers of synguanol were prepared by hydrolysis of the corresponding enantiomers of compound 1 (B=2-amino-6-chloropurin-N$^9$-yl) as described for racemic synguanol in Example 8.

R-(−)-enantiomer of synguanol 1 (B=guanin-N$^9$-yl).
  HPLC: t$_R$=6.28 min, purity 99.4%, 98.4% ee.
  Mp. >300° C.
  [α]$_D^{25}$=−83.60, c 0.11 (DMF).
  UV (ethanol) max 271 nm (ε 10,500), 229 nm (ε 26,500).
  $^1$H NMR and MS were identical to those reported for the racemic compound 1 (B=guanin-N$^9$-yl, Example 8).
  Calculated for C$_{10}$H$_{11}$N$_5$O$_2$×0.1H$_2$O: C, 51.10; H, 4.80; N, 29.80. Found: C, 51.24; H, 5.07; N, 29.65.

S-(+)-enantiomer of synguanol (1, B=guanin-N$^9$-yl).
  HPLC: t$_R$=3.85 min, purity 100%, 95.2% ee.
  Mp. >300° C.
  [α]$_D^{25}$+81.1°, c 0.11 (DMF).
  UV (ethanol) max 271 nm (ε 10,600), 230 nm (ε 27,000).
  $^1$H NMR and MS were identical to those reported for the racemic compound 1 (B=guanin-N$^9$-yl, Example 8).
  Calculated for C$_{10}$H$_{11}$N$_5$O$_2$×0.1H$_2$O: C, 51.10; H, 4.80; N, 29.80. Found: C, 50.96; H, 5.17; N, 29.77.

R- and S-enantiomers of compound 1 (B=2,6-diaminopurin-N$^9$-yl) were prepared by ammonolysis of the corresponding enantiomers of 1 (B=2-amino-6-chloropurin- $N^9$-yl) as described in Example 9 for the corresponding racemic derivative.

R-(−)-enantiomer of compound 1 (B=2,6-diaminopurine).
HPLC: $t_R$=7.00 min, purity 100%, 98.8% ee.
Mp. 236–239° C.
$[\alpha]_D^{25}$=−81.20, c 0.31 (DMF).
UV (ethanol) max 280 nm ($\epsilon$ 12,600), 219 nm ($\epsilon$ 37,200).
$^1$H NMR and MS were identical to those reported for the racemic compound 1 (B=2,6-diaminopurin-$N^9$-yl) in Example 9.
HRMS: Calculated M for $C_{10}H_{12}N_6O$ 232.1072; found 232.1071.
Calculated for $C_{10}H_{12}N_6O$: C, 51.70; H, 5.21; N, 36.20. Found: C, 51.59; H, 5.34; N, 36.27.

S-(+)-enantiomer of compound 1 (B=2,6-diaminopurine).
HPLC: $t_R$=5.35 min, purity 99.9%, 94.0% ee.
Mp. 235–238° C.
$[\alpha]_D^{25}$=+78.0°, c 0.32 (DMF).
UV (ethanol) max 280 nm ($\epsilon$ 13,000), 219 ($\epsilon$ 38,400).
$^1$H NMR and MS were identical to those reported for the racemic compound 1 (B=2,6-diaminopurin-$N^9$-yl) in Example 9.
HRMS: Calculated M for $C_{10}H_{12}N_6O$ 232.1072; found 232.1069.
Calculated for $C_{10}H_{12}N_6O$: C, 51.70; H, 5.21; N, 36.20. Found: C, 51.47; H, 4.95; N, 36.45.

R- and S-enantiomers of compound 1 (B=2-amino-6-cyclopropylamino-purin-$N^9$-yl) were prepared by reaction of the corresponding enantiomers of 1 (B=2-amino-6-chloropurin-$N^9$-yl) with cyclopropylamine as described in Example 10 for the corresponding racemic derivative.

R-(−)-enantiomer of compound 1 (B=2-amino-6-cyclopropylamino-purin-$N^9$-yl).
HPLC: $t_R$=13.68 min, purity 100%, 98.7% ee.
Mp. 185–188° C.
$[\alpha]_D^{25}$=74.5°, c 0.30 (DMF).
UV (ethanol) max 285 nm ($\epsilon$ 16,800), 224 nm ($\epsilon$ 40,500).
$^1$H NMR and MS were identical to that reported for the racemic compound 1 (B=2-amino-6-cyclopropylamino-$N^9$-yl) in Example 10.
HRMS Calcd M for $C_{13}H_{16}N_6O$ 272.1386; Found 272.1382. Anal. Calcd for $C_{13}H_{16}N_6O$: C, 57.32; H, 5.93; N, 30.87. Found: C, 57.14; H, 6.05; N, 30.84.

S-(+)-Enantiomer of Compound 1 (B=2-amino-6-cyclopropylamino-purin-$N^9$-yl).
HPLC: $t_R$=6.80 min, purity 99.1%, 94.5% ee.
Mp. 185–188° C.
$[\alpha]_D^{25}$=+73.5°, c 0.31 (DMF).
UV max 285 nm ($\epsilon$ 16,500), 223 nm ($\epsilon$ 40,500).
$^1$H NMR and MS were identical to that reported for the racemic compound 1 (B=2-amino-6-cyclopropylaminopurin-$N^9$-yl) in Example 10.
HRMS: Calculated M for $C_{13}H_{16}N_6O$ 272.1386; found 272.1385.
Calculated for $C_{13}H_{16}N_6O$: C, 57.32; H, 5.93; N, 30.87. Found: C, 57.52; H, 5.84; N, 31.01.

R-(−)-enantiomer of compound 1 (B=2-amino-6-methoxypurin-$N^9$-yl).
HPLC: $t_R$=24.80 min, purity 99.9%, 98.5% ee.
Mp. 174–176° C.
$[\alpha]_D^{25}$=−75.4°, c 0.30 (DMF).
UV max 279 nm ($\epsilon$ 11,600), 225 nm ($\epsilon$ 31,100).
$^1$H NMR and MS were identical to that reported for the racemic compound 1 B=2-amino-6-methoxypurin-$N^9$-yl) in Example 18.
HRMS Calculated M for $C_{11}H_{13}N_5O_2$ 247.1069; found 247.1067. Calculated for $C_{13}H_{16}N_6O$: C, 53.42; H, 5.30; N, 28.33. Found: C, 53.22; H, 4.99; N, 28.19.

S-(+)-enantiomer of compound 1 (B=2-amino-6-methoxypurin-$N^9$-yl).
HPLC: $t_R$=5.32 min, purity 98.5%, 94.9% ee.
Mp. 175–178° C.
$[\alpha]_D^{25}$=+74.0°, c 0.30 (DMF).
UV max 279 nm ($\epsilon$ 11,800), 224.5 ($\epsilon$ 31,500).
$^1$H NMR and MS were identical to that reported for the racemic compound 1 (B=2-amino-6-methoxypurin-$N^9$-yl) in Example 18.
HRMS: Calculated M for $C_{11}H_{13}N_5O_2$ M 247.1069; found 247.1066. Calcd for $C_{13}H_{16}N_6O$: C, 53.42; H, 5.30; N, 28.33. Found: C, 53.16; H, 5.24; N, 28.31.

EXAMPLE 23

Synthesis of (R)-(−)-Synadenol 1 (B=adenin-$N^9$-yl) and (S)-(+)-Synhypoxanthol (1, B=hypoxanthin-$N^9$-yl).

A suspension of racemic synadenol (1, B=adenin-$N^9$-yl, 200 mg, 0.92 mmol) from Example 5 in 0.05 M $Na_2HPO_4$ (pH 7.5, 100 mL) was briefly sonicated. Adenosine deaminase from calf intestine (Type II, Sigma Chemical Co., St. Louis, Mo., 30 mg, 45 units) was added and the mixture was stirred at room temperature. The progress of the reaction was followed by TLC in dichloromethane—methanol (9:1). The deamination stopped after 72 h and the ratio of synadenol (1, B=adenin-$N^9$-yl): synhypoxanthol (1, B=hypoxanthin-$N^9$-yl) was 7:3 as determined by UV spectrophotometry of the eluted spots. Addition of another two portions of enzyme (30 mg every 24 h) did not improve this ratio. The mixture was lyophilized and the resultant product was sonicated with several portions of dichloromethane—methanol (1:1, first 100 mL and then 40 mL) until no UV absorption was detectable in the solvent. The filtrate and washings were combined and evaporated. The residue was adsorbed on silica gel (4 g) and loaded on a column made of the same material. Chromatography using dichloromethane—methanol (9:1) as an eluent afforded (R)-(−)-synadenol (1, B=adenin-$N^9$-yl), 135 mg, 66.5%), $[\alpha]_D^{25}$ 59.1° (c 0.04, MeOH) and elution with dichloromethane—methanol (4:1) gave (S)-(+)-synhypoxanthol (1, B=hypoxanthin-$N^9$-yl), 85 mg, $[\alpha]_D^{25}$ 91.8° (c 0.1, MeOH).

The obtained (R)-(−)-synadenol (1, B=adenin-$N^9$-yl, 135 mg, 0.62 mmol) was subjected to a second round of deamination (60 mg, 90 units of enzyme) under the conditions described above. TLC showed a ratio of synadenol (1, B=adenin-$N^9$-yl): synhypoxanthol (1, B=hypoxanthin-$N^9$-yl) as 7:3 after 40 h. Prolonged reaction time did not improve the conversion. Work-up followed by chromatography as described above gave optically enriched (R)-(−)-synadenol (1, B=adenin-$N^9$-yl), 95 mg, 47.5%, $[\alpha]_D^{25}$ −112.0° (c 0.095, MeOH) and (S)-(+)-synhypoxanthol (1, B=hypoxanthin-$N^9$-yl), 40 mg, $[\alpha]_D^{25}$ 89.00 (c 0.1, MeOH). The combined portions of the latter product (125 mg) were rechromatographed on silica gel using dichloromethane—methanol (4:1) to afford optically pure (S)-(+)-synhypoxanthol (1, B=hypoxanthin-$N^9$-yl), 96 mg, 47.8%, as a white solid.

Mp. 235–240° C.
$[\alpha]_D^{25}$ 112.5°(c 0.08, MeOH).
UV (ethanol) max 228 nm ($\epsilon$ 31,300).
IR (KBr): 3450 $cm^{-1}$ (OH), 1600 and 1670–1690 $cm^{-1}$ (purine ring and olefin), 1040 $cm^{-1}$ (cyclopropane ring).
$^1$H NMR ($CD_3SOCD_3$) $\partial$ 1.21 (ddd, 1) and 1.48 (td, 1, $H_4$·), 2.12 (dqd, 1, $H_3$·), 3.28 (dt, overlapped with $H_2O$, 1) and 3.72 (dd, 1, $H_5$·), 5.09 (t, 1, OH), 7.33 (d, 1, $H_1$·), 8.07 (s, 1, $H_2$), 8.69 (s, 1, $H_8$), 12.41 (s, 1, NH).

$^{13}$C NMR (CD$_3$SOCD$_3$) ppm: 6.67 (C$_{4'}$), 19.62 (C$_{3'}$), 63.11 (C$_{5'}$), 110.50 (C$_{1'}$), 117.58 (C$_{2'}$), 124.18 (C$_5$), 137.56 (C$_8$), 146.61 (C$_2$), 147.19 (C$_4$), 156.97 (C$_6$).

EI-MS 217 (M-H, 26.3), 200 (58.6), 187 (40.5), 159 (11.7), 148 (16.1), 135 (100.0).

Calculated for C$_{10}$H$_{10}$N$_4$O$_2$ 0.6H$_2$O: C, 52.44; H, 4.93; N, 24.46. Found: C, 52.00; H, 4.57; N, 24.74.

In another experiment, racemic synadenol (1, B=adenin-N$^9$-yl), 450 mg, 2.07 mmol furnished optically enriched (R)-(−)-enantiomer 1 (B=adenin-N$^9$-yl, 200 mg, 44.4%) and (S)-(+)-synhypoxanthol (1, B=hypoxanthin-N$^9$-yl), 200 mg, 44.4%. The combined portions of optically enriched (R)-(−)-synadenol (1, B=adenin-N$^9$-yl), 280 mg, 1.29 mmol) from both experiments were incubated with adenosine deaminase (100 mg, 150 units) in phosphate buffer (250 mL) as described above. The ratios of synadenol (1, B=adenin-N$^9$-yl): synhypoxanthol (1, B=hypoxanthin-N$^9$-yl) were 94:6 after 24 h and 93:7 after 48 h. Work-up and purification as described above gave optically pure (R)-(−)-synadenol (1, B=adenin-N$^9$-yl), 250 mg, 38.5% overall yield based on racemic synadenol (1, B=adenin-N$^9$-yl), 650 mg, 2.99 mmol.

HPLC (see Example 22): t$_R$ 10.99 min., 96% ee.

Mp. 237–238° C.

$[\alpha]^{25}_D$ −120.00 (c 0.075, methanol).

UV (ethanol) max 277 nm (shoulder, ε 8,800), 260 nm (ε 12,300), 227 nm (ε 26,900).

IR, $^1$H NMR and EI-MS were identical to the racemic syandenol (1, B=adenin-N$^9$-yl) in Example 5.

Calculated for C$_{10}$H$_{11}$N$_5$O: C, 55.29; H, 5.10; N, 32.24. Found: C, 55.02; H, 5.03; N, 32.32.

Optically enriched (S)-(+)-synhypoxanthol (1, B=hypoxanthin-N$^9$-yl), 20 mg, 7.1%, $[\alpha]^{25}_D$ 60.60 (c 0.11, methanol), was also obtained.

EXAMPLE 24

Synthesis of (S)-(+)-Synadenol (1, B=adenin-N$^9$-yl) (S)-(+)-5'—O-Acetylsynhypoxanthol.

A mixture of (S)-(+)-synhypoxanthol (1, B=hypoxanthin-N$^9$-yl), 31 mg, 0.6 mmol and acetic anhydride (1.0 mL, 10.6 mmol) in pyridine (10 mL) was stirred at room temperature for 16 h. Volatile components were removed in vacuo and the residue was passed through a short silica gel column using dichloromethane—methanol (92:8) as an eluent to give (S)-(+)-O-acetyl-(+)-synhypoxanthol (1, B=hypoxanthin-N$^9$-yl), 155 mg, 99%.

Mp. 234–237° C.

$[\alpha]25_D$ +108.6°, c 0.084 (MeOH).

UV (ethanol) max 227 nm (ε 27,300).

IR (KBr) 3460 and 3140 cm$^{-1}$ (NH), 1735 cm$^{-1}$ (ester), 1695 and 1595 cm$^{-1}$ (hypoxanthine ring and olefin), 1040 cm$^{-1}$ (cyclopropane).

$^1$H NMR (CD$_3$SOCD$_3$) δ 1.38 (ddd, 1) and 1.63 (td, 1, H$_{4'}$), 1.88 (s, 3, CH$_3$), 2.32 (dqd, 1, H$_{3'}$), 3.93 (dd, 1) and 4.14 (dd, 1, H$_{5'}$), 7.37 (q, 1, H$_{1'}$), 8.06 (s, 1, H$_2$), 8.36 (s, 1, H$_8$), 12.40 (bs, 1, NH).

$^{13}$C NMR (CD$_3$SOCD$_3$) ppm 7.79 (C$_{4'}$), 15.89 (CH$_3$), 20.89 (C$_{3'}$), 65.87 (C$_{5'}$), 111.56 (C$_{1'}$), 117.03 (C$_{2'}$), 124.19 (C$_5$), 137.65 (C$_8$), 146.68 (C$_2$), 147.42 (C$_4$), 156.99 (C$_6$), 170.53 (CO, acetate).

EI-MS 260 (M, 26.1), 218 (5.4), 201 (66.5), 174 (15.6), 137 (100.0).

HRMS: Calculated M for C$_{12}$H$_{12}$N$_4$O$_3$ 260.0909, found 260.0906.

Calculated for C$_{12}$H$_{12}$N$_4$O$_3$: C, 55.37; H, 4.65; N, 21.54. Found: C, 55.12; H, 4.73; N, 21.69.

(S)-(+)-syn-6-Chloro-N$^9$-(2-acetoxymethylcyclopropylidene-methyl)purine.

N,N-Dimethylaminochloromethyleneammonium chloride in chloroform (0.2 M, 3.5 mL, 8.7 mmol) was added to a suspension of (S)-(+)-5'—O-acetylsynhypoxanthol (150 mg, 0.58 mmol) in chloroform (15 mL). The mixture was refluxed for 1 h. The solvent was evaporated and the residue was chromatographed on a silica gel column using dichloromethane—methanol (96:4) to the title product (141 mg, 87.8%).

Mp. 122–125° C.

$[\alpha]^{25}_D$+93.9° (c 0.095, methanol).

UV (ethanol) max 260 nm (shoulder, ε 8,200), 228 nm (ε 28,500). IR (KBr) 1730 cm$^{-1}$ (ester), 1590 and 1563 cm$^{-1}$ (purine ring and olefin), 1030 cm$^{-1}$ (cyclopropane).

$^1$H NMR (CD$_3$SOCD$_3$) ∂ 1.40 (ddd, 1) and 1.73 (td, 1, H$_{4'}$), 2.04 (s, 3, CH$_3$), 2.26–2.37 (m, 1H, H$_{3'}$), 3.77 (dd, 1H, $^2$J=11.4 Hz, $^3$J=8.7 Hz) and 4.53 (dd, 1, H$_{5'}$), 7.55 (q, 1, H$_{1'}$), 8.74 and 8.76 (2s, 1 each, H$_2$ and H$_8$).

13C NMR (CD$_3$SOCD$_3$) ppm 7.46 (C$_{4'}$), 15.98 (CH$_3$), 20.80 (C$_{3'}$), 66.36 (C$_5$), 111.11 (C$_{1'}$), 116.25 (C$_{2'}$), 131.41 (C$_5$), 142.32 (C$_8$), 150.32 (C$_4$), 151.18 (C$_2$), 152.44 (C$_6$), 170.56 (CO, acetate).

EI-MS 280 and 278 (M, 7.3, 22.0), 238 and 236 (2.6, 7.9), 221 and 219 (36.2, 81.1), 207 (8.9), 183 (8.4), 157 and 155 (29.4, 85.9), 82 (63.0), 43 (100.0).

HRMS: Calculated M for C$_{12}$H$_{11}$ClN$_4$O$_2$ 278.05705, found: 278.0568.

Calculated for C$_{12}$H$_{11}$ClN$_4$O$_2$: C, 51.79; H, 3.99; N, 20.14; Cl, 12.58. Found: C, 51.86; H, 3.99; N, 20.06; Cl, 12.60.

(S)-(+)-Synadenol (1, B=adenin-N$^9$-yl).

A mixture of (S)-(+)-syn-6-chloro-N$^9$-(2-acetoxymethylcyclopropylidene-methyl)-purine (130 mg, 0.47 mmol) in methanolic ammonia (20%, 70 mL) was heated in a stainless steel bomb at 100° C. for 18 h. After cooling, the contents were evaporated. The residue was chromatographed on a silica gel column using dichloromethane—methanol (9:1→85:15) to give (S)-(+)-synadenol (1, B=adenin-N$^9$-yl), 91 mg, 90% after drying at <0.01 mmHg and 100° C. for 2 h.

HPLC (see Example 22): t$_R$ 10.25 min., 96% ee.

Mp. 233–235° C. (modification change between 213 and 230° C.).

$[\alpha]^{25}_D$ +123.00, c 0.073 (methanol).

UV (ethanol) max 277 nm (shoulder, ε 8,600), 261 nm (ε 12,200), 227 nm (ε 26,700).

IR, $^1$H NMR and MS were identical to the racemic synadenol (1, B=adenin-N$^9$-yl) in Example 5.

Calculated for C$_{11}$H$_{11}$N$_5$O: C, 55.29; H, 5.10; N, 32.24. Found: C, 55.15; H, 5.20; N, 32.33.

EXAMPLE 25

Synthesis of Methyl Phenylphosphoro-L-alaninates of R- and (S)-syn-2,3-diamino-N$^9$-(2-hydroxycyclopropylidene-methyl)purine (3, B=2,6-diaminopurin-N$^9$-yl).

"R" Diastereoisomers:

The procedure described in Example 15 was followed with (R)-(−)-syn-2,6-di-aminopurine analog 1 (B=2,6-diaminopurin-N$^9$-yl) from Example 22 as a starting material.

Mp 75–86° C.

UV (ethanol) max 281 nm (ε 12,670), 218 nm (ε 38,930).

$^1$H NMR (CD$_3$SOCD$_3$) ∂ 1.15 (d, 3, CH$_3$), 1.27–1.38 (m, 1) and 1.50–1.62 (qd, 1, $H_{4'}$), 2.22–2.40 (m, 1H, $H_{3'}$), 3.52 and 3.55 (2s, 3, $OCH_3$), 3.68–3.88 (m, 1, CH of alanine), 3.90–4.05 (m, 1) and 4.10–4.30 (m, 1, $H_{5'}$), 5.91 (s, 2, 2—$NH_2$), 5.97 (dq, 1, NH of alanine), 6.79 (s, 2, 6—$NH_2$), 7.08–7.20 (m, 3) and 7.27–7.36 (m, 2, phenyl), 7.21–7.27 (m, 1, $H_{1'}$), 8.03 and 8.06 (2s, 1, $H_8$).

$^{13}C$ NMR ($CD_3SOCD_3$) ppm 7.62 ($C_{4'}$), 17.32 and 17.41 ($C_{3'}$), 68.45 ($C_{5'}$), 111.81 ($C_{1'}$), 113.28 ($C_{2'}$); alanine: 19.97 and 20.06 ($CH_3$), 50.21 and 50.24 (CH), 52.24 ($OCH_3$), 174.20 (C=O); phenyl: 120.65 (C-meta), 124.94 (C-ortho), 130.00 (C-para), 151.08 (C-ipso); purine: 112.18 ($C_5$), 134.58 ($C_8$), 150.96 ($C_4$), 156.61 ($C_2$), 161.10 ($C_6$).

Calculated for $C_{20}H_{24}N_7O_5P$: C, 50.72; H, 5.11; N, 20.72. Found: C, 50.35; H, 5.10; N, 20.88.

"S" Diastereoisomers:

The procedure described in Example 15 was followed with (S)-(−)-syn-2,6-di-aminopurine analog 1 (B=2,6-diaminopurin-$N^9$-yl) from Example 22 as a starting material.

Mp. 74–84° C.

UV (ethanol) max 281 nm (ε 12,420), 218 nm (ε 38,200).

$^1H$ NMR ($CD_3SOCD_3$) a 1.14 and 1.19 (2d, 3, $CH_3$), 1.27–1.38 (m, 1) and 1.51–1.62 (m, 1, $H_{4'}$), 2.22–2.40 (m, 1, $H_{3'}$), 3.52 and 3.55 (2s, 3, $OCH_3$), 3.694.06 (m, 2) and 4.154.28 (m, 1, CH of alanine and $H_{5'}$), 5.92 (s, 2, 2—$NH_2$), 5.97 (ddd, 1, NH of alanine), 6.80 (s, 2, 6—$NH_2$), 7.08–7.20 (m, 3) and 7.27–7.36 (m, 2, phenyl), 7.21–7.27 (m, 1H, $H_{1'}$), 8.04 and 8.05 (2s, 1H, $H_8$).

$^{13}C$ NMR ($CD_3SOCD_3$) ppm 7.62 ($C_{4'}$), 17.37 and 17.43 ($C_{3'}$), 68.42 and 68.47 ($C_{5'}$), 111.79 ($C_{1'}$), 113.27 ($C_{2'}$); alanine: 20.01 and 20.12 ($CH_3$), 50.08 and 50.16 (CH), 52.29 ($OCH_3$), 174.13 (C=O); phenyl: 120.62 and 120.67 (C-meta), 124.92 (C-ortho), 129.99 (C-para), 151.06 (C-ipso); purine: 112.22 ($C_5$), 134.62 ($C_8$), 150.92 ($C_4$), 156.63 ($C_2$), 161.10 ($C_6$).

Calculated for $C_{20}H_{24}N_7O_5P$: C, 50.72; H, 5.11; N, 20.72. Found: C, 50.56; H, 5.28; N, 20.82.

EXAMPLE 26

In vitro Antiviral Activity

In vitro antiviral activity was determined using the methods described in Example 16. The R- and S-enantiomers of the compounds of Formula 1 were synthesized and their antiviral activity against HCMV, HSV-1 and HSV-2 in vitro was investigated. The enantioselectivity of the antiviral effect depends on the type of the heterocyclic base and virus involved. Both enantiomers of adenine analogue (B=adenine) were equipotent against HCMV ($EC_{50}$ 2.4 and 2.9 μM, respectively) whereas the S-enantiomers of the rest of the group were strongly preferred ($EC_{50}$ 1.8–21 PM) over R-enantiomers (30–>100 μM) (the S-enantiomers were the most effective agents in the HSV-1 assay of active analogues).

Two racemic analogues of Formula 1, B=2-amino-6-methoxypurine and B=2-amino-6-azidopurine were assayed for antiviral activity. Both showed good activity against HCMV, while only the B=2-amino-6-methoxypurine showed any significant activity against HSV-1.

Antiviral Activity:

| Compound | $IC_{50(\mu M)}$ | | |
|---|---|---|---|
| | HCMV[a] | HSV-1[b] | HIV-1[c] |
| 1 (B = 2-amino-6-methoxypurine), Example 18 | 3.1 | 33 | >100 |
| 1 (B = 2-amino-6-azidopurine), Example 19 | 41 | >100 | >100 |
| R-1 (B = adenine), Example 23 | 2.9 | 38 | 7 |
| S-1 (B = adenine), Example 24 | 2.4 | 8.8 | 1.2 |
| R-1 (B = 2-amino-6-chloropurine), Example 22 | 30 | >100 | >100 |
| S-1 (B = 2-amino-6-chloropurine), Example 22 | 1.8 | 45 | >100 |
| R-1 (B = guanine), Example 22 | >100 | >100 | >100 |
| S-1 (B = guanine), Example 22 | 2.5 | 45 | >100 |
| R-1 (B = 2,6-diaminopurine), Example 22 | >100 | >100 | >100 |
| S-1 (B = 2,6-diaminopurine), Example 22 | 21 | >100 | >100 |
| R-1 (B = 2-aminopurine-6-cyclopropylaminopurine), Example 22 | >100 | >100 | >100 |
| S-1 (B = 2-aminopurine-6-cyclopropylaminopurine), Example 22 | 1.8 | 20 | 65 |
| R-1 (B = 2-amino-6-methoxy-purine), Example 22 | >100 | >100 | >100 |
| S-1 (B = 2-amino-6-methoxy-purine), Example 22 | 2.5 | 20 | 42 |
| "R"-diastereoisomers, Example 25 | 23 | 70 | 0.55 |
| "S"-diastereoisomers, Example 25 | 3 | 40 | 3.5 |

[a]Plague reduction.
[b]ELISA.
[c]Reverse transcriptase assay. Data for high multiplicity of infection (moi). The $IC_{50}$ values in table on page 36 refer to low moi.

Compounds of the present invention were also tested for cytotoxicity in a culture of HFF and KB cells according to the methods in Example 16.

Cytotoxicity:

| Enantiomer | $IC_{50(\mu M)}$o | | |
|---|---|---|---|
| | HFF (visual) | KB (growth) | CEM (visual) |
| 1 (B = 2-amino-6-methoxypurine), Example 18 | >100 | >100 | >100 |
| 1 (B = 2-amino-6-azidopurine), Example 19 | >100 | >100 | >100 |
| R-1 (B = adenine), Example 23 | >100 | >100 | >100 |
| S-1 (B = adenine), Example 24 | 100 | 80 | >100 |
| R-1 (B = 2-amino-6-chloropurine), Example 22 | 32 | >100 | >100 |
| S-1 (B = 2-amino-6-chloropurine), Example 22 | >100 | >100 | >100 |
| R-1 (B = guanine), Example 22 | >100 | >100 | >100 |
| S-1 (B = guanine), Example 22 | >100 | >100 | >100 |
| R-1 (B = 2,6-diaminopurine), Example 22 | >100 | >100 | >100 |
| S-1 (B = 2,6-diaminopurine), Example 22 | 21 | >100 | >100 |
| R-1 (B = 2-aminopurine-6-cyclopropylaminopurine), Example 22 | >100 | >100 | >100 |
| S-1 (B = 2-aminopurine-6-cyclopropylaminopurine), Example 22 | >100 | >100 | >100 |
| R-1 (B = 2-amino-6-methoxypurine), Example 22 | >100 | >100 | >100 |
| S-1 (B = 2-amino-6-methoxypurine), Example 22 | >100 | >100 | >100 |
| "R"-diastereoisomers, Example 25 | 100 | >100 | >100 |
| "S"-diastereoisomers, Example 25 | 100 | 40 | 32 |

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings and specification.

All patents and other publications cited herein are expressly incorporated by reference.

We claim:

1. A compound having the formula:

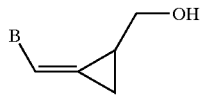

wherein B is a purine moiety, and pharmaceutically acceptable salts, and prodrugs, thereof.

2. A compound having the formula:

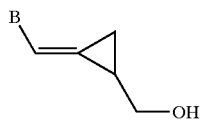

wherein B is a purine moiety, and pharmaceutically acceptable salts, and prodrugs, thereof.

3. The compound of claim 1 or 2, wherein B is selected from the group consisting of 6-aminopurine, 2,6-diaminopurine, 2-ammo-6-cyclopropylaminopurine, 6-hydroxypurine, 2-amino-6-halo substituted purine, 2-amino-6-alkoxy substituted purine, and 2-amino-6-hydroxypurine.

4. The compounds of claim 1 or 2, wherein B is selected from the group consisting of adenin-$N^9$-yl, guanin-$N^9$-yl, 2,6-diaminopurine-$N^9$-yl, 2-amino-6-cyclopropylaminopurin-$N^9$-yl and 2-amino-6-chloropurin-$N^9$-yl.

5. An antiviral compound selected from the group consisting of syn-$N^9$-2-hydroxymethylcyclo-propylidenemethyl)adenine, syn-$N^9$-2-hydroxymethyl-cyclopropylidenemethyl)guanine, syn-2,6-diamino-$N^9$-2-hydroxymethylcyclo-propylidenemethyl)purine, syn-2-amino-6-cyclopropylamino-$N^9$-2-hydroxymethyl-cyclopropylidenemethyl)purine and pharmaceutically acceptable salts, and prodrugs, thereof.

6. An antiviral compound selected from the group consisting of methyl-phenyl-phosphoro-L-alaninate of syn-$N^9$-(2-hydroxymehylcyclo-propylidenemethyl)adenine, methyl phenyl-phosphoro-L-alaninate of anti $N^2$-(2-hydroxymethylcyclo-proylidenemethyl pharmaceutically acceptable salts, and prodrugs, thereof.

7. A composition comprising a compound of claim 1 or 2 and a pharmaceutically acceptable carrier.

8. A method of treating mammals infected with a virus selected from the group consisting of HCMV, HSV-1, HSV-2, HHV-6, HIV, EBV, and HBV comprising the step of administering to the mammal an antiviral compound selected from the group consisting of the compounds of claim 1 or 2.

9. The method of claim 8, wherein said mammal is a human.

10. The method of claim 8, wherein said virus is a human herpes virus.

11. The method of claim 8, wherein said virus is a human immunodeficiency virus.

12. The method of claim 8, wherein said virus is hepatitis B virus.

13. The method of claim 8, further comprising the step of administering an additional antiviral compound.

14. The method of claim 13, wherein the additional antiviral compound is selected from the group consisting of acyclovir, ganciclovir, zidovudine, AZT, ddl, ddC, d4T, and combinations thereof.

15. The compound having the formula:

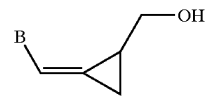

wherein B is 2-amino-6-cyclopropylaminopurin-$N^9$-yl, and pharmaceutically acceptable salts, and prodrugs thereof.

16. The (S)-(+)-enanitomer of the compound of claim 15.

17. The (R)-(−)-enanitomer of the compound of claim 15.

18. A composition comprising a compound of claims 15, 16 or 17 and a pharmaceutically acceptable carrier.

19. A method of treating mammals infected with a virus selected from the group consisting of HCMV, HSV-1, HSV-2, HHV-6, HIV, EBV, and HBV comprising the step of administering to the mammal an antiviral compound selected from the group consisting of the compounds of claim 15, 16, or 17.

* * * * *

UNITED STATES PATENT AND TRADEMARK OFFICE
CERTIFICATE OF CORRECTION

PATENT NO.    : 6,790,841 B2
DATED         : September 14, 2004
INVENTOR(S)   : Jiri Zemlicka et al.

It is certified that error appears in the above-identified patent and that said Letters Patent is hereby corrected as shown below:

<u>Column 38,</u>
Line 2, replace "proylidenemethyl" with -- propylidenemethyl) --.
Line 2, after "propylidenemethyl)" insert -- adenine and --.
Line 34, after "prodrugs" insert -- , --.

Signed and Sealed this

Eighteenth Day of January, 2005

JON W. DUDAS
*Director of the United States Patent and Trademark Office*